US008871893B2

(12) United States Patent
Phillips et al.

(10) Patent No.: US 8,871,893 B2
(45) Date of Patent: Oct. 28, 2014

(54) SIGNAL-RESPONSIVE PLASTICS

(75) Inventors: Scott T. Phillips, State College, PA (US); Wanji Seo, State College, PA (US); Jessica Robbins, State College, PA (US); Michael Olah, State College, PA (US); Kyle Schmid, Riverside, PA (US); Anthony Michael DiLauro, Warwick, RI (US)

(73) Assignee: The Penn State Research Foundation, University Park, PA (US)

( * ) Notice: Subject to any disclaimer, the term of this patent is extended or adjusted under 35 U.S.C. 154(b) by 712 days.

(21) Appl. No.: 13/104,553

(22) Filed: May 10, 2011

(65) Prior Publication Data
US 2014/0242623 A1    Aug. 28, 2014

Related U.S. Application Data

(60) Provisional application No. 61/332,936, filed on May 10, 2010.

(51) Int. Cl.
| C08G 63/00 | (2006.01) |
| C09J 161/02 | (2006.01) |
| C09D 161/02 | (2006.01) |
| C08F 20/44 | (2006.01) |
| C12Q 1/34 | (2006.01) |
| C08G 6/00 | (2006.01) |
| G01N 31/22 | (2006.01) |
| C08G 63/91 | (2006.01) |
| C08F 26/06 | (2006.01) |
| C08F 20/56 | (2006.01) |
| C08F 12/08 | (2006.01) |
| C08F 20/10 | (2006.01) |
| C08G 63/02 | (2006.01) |

(52) U.S. Cl.
CPC ............ *C08G 6/00* (2013.01); *C09J 161/02* (2013.01); *C09D 161/02* (2013.01); *C08F 20/44* (2013.01); *C12Q 1/34* (2013.01); *G01N 31/22* (2013.01); *C08G 63/91* (2013.01); *C08F 26/06* (2013.01); *C08F 20/56* (2013.01); *C08F 12/08* (2013.01); *C08F 20/10* (2013.01)
USPC ........................................................ 528/176

(58) Field of Classification Search
USPC ........................................................... 528/176
See application file for complete search history.

(56) References Cited

U.S. PATENT DOCUMENTS

| 4,734,481 A | 3/1988 | Steinmann |
| 4,820,829 A | 4/1989 | Steinmann |
| 7,625,764 B2 | 12/2009 | Stayton et al. |
| 2008/0153035 A1 | 6/2008 | Abdallah et al. |
| 2008/0269460 A1 | 10/2008 | Bowman et al. |

FOREIGN PATENT DOCUMENTS

| WO | 2004/071644 A2 | 8/2004 |
| WO | 2008053479 A1 | 5/2008 |

OTHER PUBLICATIONS

International Search Report for PCT/US2011/035927 dated Jan. 19, 2012 (Form PCT/ISA/210).
Written Opinion of the International Searching Authority dated Jan. 19, 2012 (Form PCT/ISA/237).
Köstler et al., "Amphiphilic Block Copolymers containing Thermally Degradable Poly(phthalaldehyde) Blocks", Journal of Polymer Science Part A: Polymer Chemistry, Mar. 15, 2009, vol. 47, Issue 6, pp. 1499-1509.
Tsuda et al., Acid-catalyzed Degradation Mechanism of Poly(phthalaldehyde): Unzipping Reaction of Chemical Amplification Resist, Journal of Polymer Science Part A: Polymer Chemistry, Jan. 1, 2000, vol. 35, Issue 1 (entire document).
Tsuda et al., "Acid-Catalyzed Degradation Mechanism of Poly(phthalaldehyde): Unzipping Reaction of Chemical Amplification Resist", Journal of Polymer Science Part A., Polymer Chemistry 1997, vol. 35, pp. 77-89.
Shabat et al., "Chemical Adaptor Systems", Chem. Eur. J. 2004, vol. 10, pp. 2626-2634.
Dewit et al., "A Cascade Biodegradable Polymer Based on Alternating Cyclization and Elimination Reactions", J. Am. Chem. Soc. 2009, vol. 131, pp. 18327-18334.
Esser-Kahn et al., "Programmable Microcapsules from Self-Immolative Polymers", J. Am. Chem. Soc. 2010, vol. 132, pp. 10266-10268.
Knoll et al., "Probe-Based 3-D Nanolithography Using Self-Amplified Depolymerization Polymers", Adv. Mater. 2010 vol. 22, pp. 3361-3365.
Ortiz et al., "Improved Iterative Synthesis of Linearly Disassembling Dendrons", J. Org. Chem. 2010, vol. 75, pp. 6154-6162.
Kevwitch et al., "Synthesis and Degradation of Photolabile Dendrimers based on O-nitrobenzyl Ether Photolabile Cores†", New J. Chem. 2007, vol. 31, pp. 1332-1336.
Szalai et al., "Phototriggering of Geometric Dendrimer Disassembly: an Improved Synthesis of 2,4-bis (hydroxymethyl)phenol Based Dendrimers", Tetrahedron 2004, vol. 60, pp. 7261-7266.

(Continued)

*Primary Examiner* — Terressa Boykin
(74) *Attorney, Agent, or Firm* — Buchanan Ingersoll & Rooney PC

(57) ABSTRACT

We disclose methods and compositions for preparation of stimuli-responsive plastics that are capable of responding to chemical and/or physical signals in their environment. In one embodiment the plastics consist of patterned mixtures of poly(phthalaldehyde) polymers in which each polymer contains a different end-capping group (also called a "trigger"), responsive to a different signal. Other embodiments use different polymers and different triggers. The plastics may be homogeneous in composition, but each polymer within the plastic is capable of responding to a different signal and depolymerizing once this signal reacts with the trigger. This process of depolymerization enables the plastic to alter its physical features non-linearly to external signals: i.e., the degree of change in physical form is much larger than the intensity of the initial signal.

17 Claims, 15 Drawing Sheets

(56) References Cited

OTHER PUBLICATIONS

Szalai et al., "Geometric Disassembly of Dendrimers: Dendritic Amplification", J. Am. Chem. Soc. 2003, vol. 125, pp. 15688-15689.

Li et al., "Dendrimer Disassembly by Benzyl Ether Depolymerization", J. Am. Chem. Soc. 2003, vol. 125, 10516-10517.

Polaske et al., "Convergent Synthesis of Geometrically Disassembling Dendrimers using Cu(I)-Catalyzed C—O Bond Formation", Org. Lett. 2010, vol. 12, No. 21, pp. 4944-4947.

Zhang et al., "Phosphazene Bases: A New Category of Organocatalysts for the Living Ring-Opening Polymerization of Cyclic Esters", Macromolecules 2007, vol. 40, pp. 4154-4158.

McGrath, Dendrimer Disassembly as a New Paradigm for the Application of Dendritic Structures, Molecular Pharmaceuticals 2005, vol. 2, No. 4, pp. 253-263.

Dickinson et al., "A New Sensitive and Specific Test for the Detection of Aldehydes: Formation of 6-Mercapto-3-substituted-s-triazolo[4,3-b]-s-tetrazines", Chemical Communications, 1970, pp. 1719-1720.

Benson et al., "o-Phthalaldehyde Fluorogenic Detection of Primary Amines in the Picomole Range, Comparison with Fluorescamine and Ninhydrin", Proc. Nat. Acad. Sci USA Feb. 1975, vol. 72, No. 2, pp. 619-622.

Montigny et al., "Naphthalene-2,3-dicarboxaldehyde/Cyanide Ion: A Rationally Designed Flourogenic Reagent for Primary Amines", Anal. Chem. 1967, vol. 59, pp. 1096-1101.

Lin et al., "Irerative Synthesis of Acenes via Homo-Elongationt†", Chem. Commun. 2009, pp. 803-805.

Coulembier et al., "Probe-Based Nanolithography: Self-Amplified Depolymerization Media for Dry Lithography", Macromolecules 2010, vol. 43, pp. 572-574.

Sagi et al., "Self-Immolative Polymers", J. Am. Chem. Soc. 2008, vol. 130, pp. 5434-5435.

a) *n*-BuLi (0.003 eq), THF, −80 °C, 10–14 days; b) allyl chloroformate, −80 °C, 72 h, 94%; c) allyl triflate, −80 °C, 96 h, 83%; d) TBSCl, −80 °C, 72 h, 86%; e) benzyl chloroformate, −80 °C, 72 h, 76%; f) methyl triflate, −80 °C, 96 h, 83%.

FIGURE 5
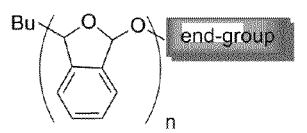
poly(phthalaldehyde)
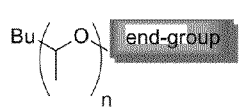
poly(acetaldehyde)
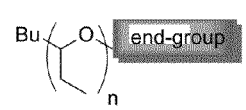
poly(propionaldehyde)
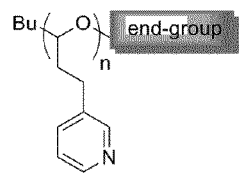
poly(3-pyridinepropanal)
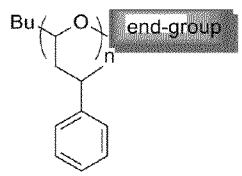
poly(β-methyl-3-pyridinepropanal)
Copolymers
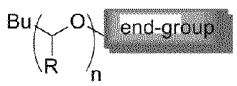
R = CH$_3$ or CH$_2$CH$_3$
acetaldehyde-propionaldehyde
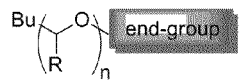
R = CH$_3$ or (CH$_2$)$_2$CH$_3$
acetaldehyde-butylaldehyde
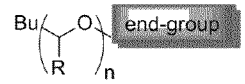
R = CH$_3$ or (CH$_2$)$_5$CH$_3$
acetaldehyde-pentanaldehyde

FIGURE 6

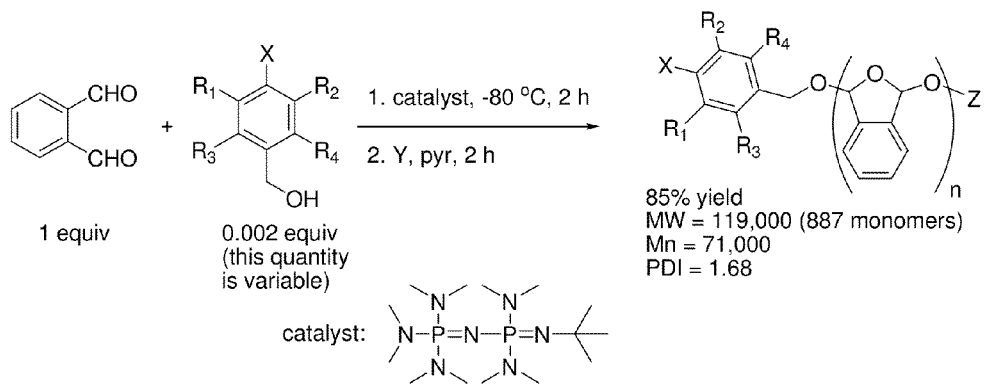

X = functionality that cleaves in the presence of a specific chemical signal.
    Examples include: $R_3SiO-$, $(RO)_2B-$, $CH_2CHCH_2OCO_2-$, monosaccharide-O-, polysaccharide-O-, and peptide-NH-.

Y = $Ac_2O$, isocyanates, alkylating reagents, acid chlorides, acid fluorides, etc.

Z = functionality arising from reaction of the polymer with Y $R_1$, $R_2$, $R_3$, and $R_4$ = H, or OMe, or O-Alkyl, or O-Aryl; including any combination of these substituents Method 1:

Y = Br or I ligand = none, Me₄Phen, or others (see reference: J. Org. Chem. 2008, 73, 284)

R = C1-C30 branched and straight-chain alkyl; benzyl; allyl; esters (e.g., $H_3CCO$); carbamates (e.g., $H_3CNHCO$)

X = functionality that cleaves in the presence of a specific chemical signal.
 Examples include: $R_3SiO-$, $(RO)_2B-$, $CH_2CHCH_2OCO_2-$, monosaccharide-O-,
 polysaccharide-O-, peptide-NH-, etc.

Method 2:

Y = Br or I

X = functionality that cleaves in the presence of a specific chemical signal.
    Examples include: $R_3SiO$-, $(RO)_2B$-, $CH_2CHCH_2OCO_2$-, monosaccharide-O-,
    polysaccharide-O-, peptide-NH-, etc.

FIGURE 14
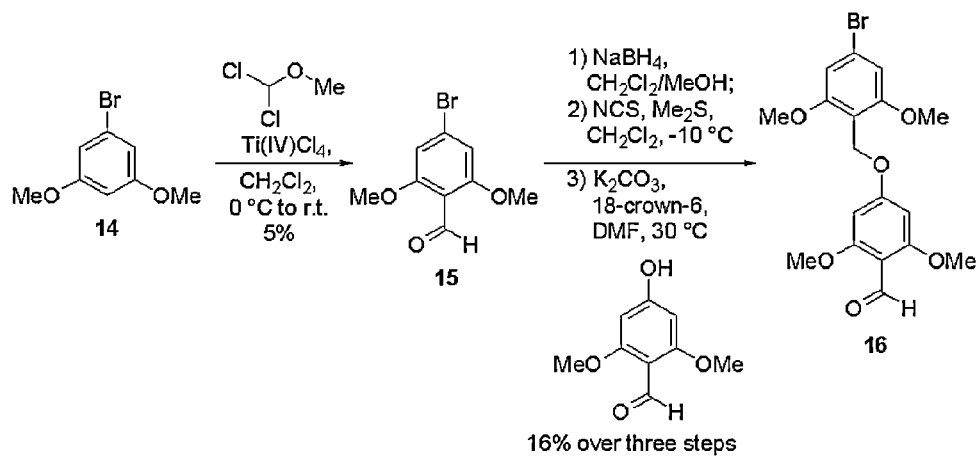
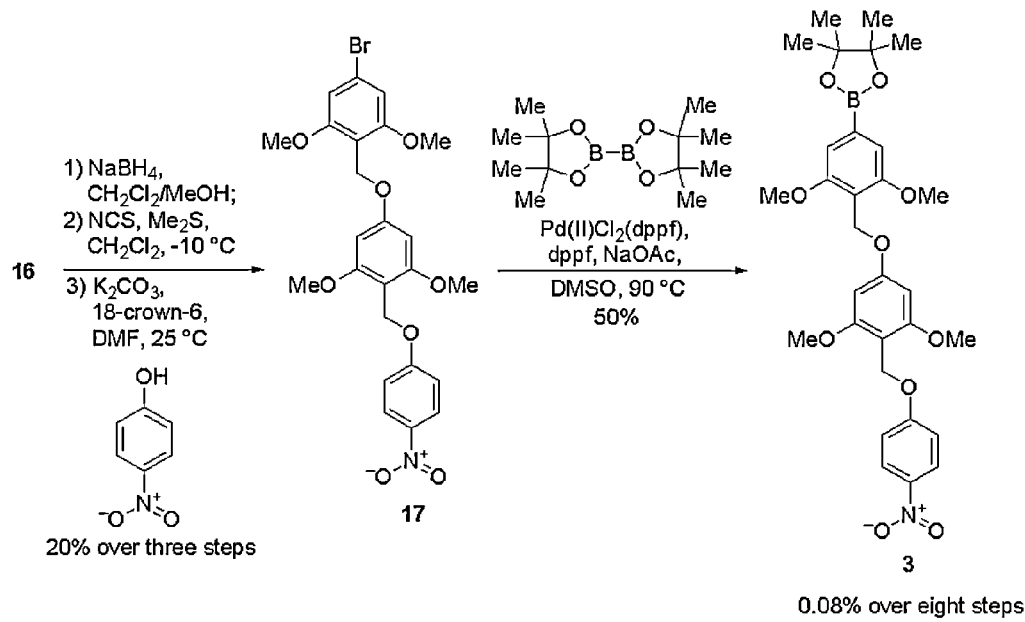

FIGURE 15

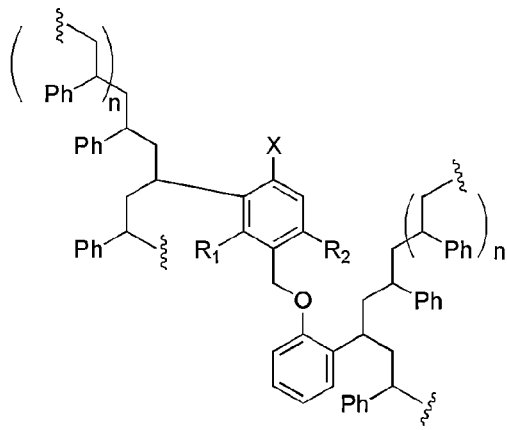

R₁, R₂ = H, or OMe, or O-Alkyl, or O-Aryl; including any combination of these substituents X = functionality that cleaves in the presence of a specific chemical signal.
  Examples include: $R_3SiO-$, $(RO)_2B-$, $CH_2CHCH_2OCO_2-$, monosaccharide-O-, polysaccharide-O-, peptide-NH-, etc.

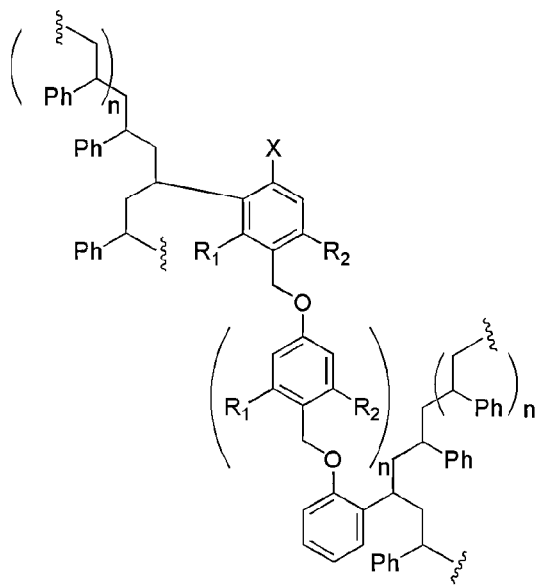

R₁, R₂ = H, or OMe, or O-Alkyl, or O-Aryl; including any combination of these substituents X = functionality that cleaves in the presence of a specific chemical signal.
  Examples include: $R_3SiO-$, $(RO)_2B-$, $CH_2CHCH_2OCO_2-$, monosaccharide-O-, polysaccharide-O-, peptide-NH-, etc.

SIGNAL-RESPONSIVE PLASTICS

CROSS-REFERENCE TO RELATED APPLICATIONS

This application claims priority to U.S. Provisional Patent Application No. 61/332,936, filed on May 10, 2011. That application is incorporated by reference herein.

STATEMENT OF FEDERALLY SPONSORED RESEARCH AND DEVELOPMENT

This invention was made with government support under Grant No. N66001-09-1-2111, awarded by DARPA. The Government has certain rights in the invention.

BACKGROUND OF THE INVENTION

1. Field of the Invention

The present subject matter relates to polymers that depolymerize autonomously in response to specific signals. Methods of use of the polymers and articles made from or including those articles are also included herein.

2. Background of the Related Art

Cells exhibit diverse responses to trace levels of external chemical and physical signals. Their response characteristics are sophisticated, sensitive, and selective, and the ability to mimic such properties with synthetic materials has been a long sought after goal in materials chemistry.1 Materials with "life-like" qualities should be useful as smart coatings, textiles, adhesives, bandages, packaging, plastics, as well as in many other applications.

Recent advances in materials chemistry have provided macroscopic materials that begin to emulate some of these basic behaviors. For example, some macroscopic materials move in response to applied chemical and physical signals, repair themselves when subjected to mechanical stresses, or change wetting properties as a function of temperature. Other macroscopic materials have shape memory, and will adopt their original shapes after being perturbed by external forces. In other cases, the physical state of a material changes (i.e., solution⇌gel) upon exposure to pH gradients (e.g., pH-responsive hydrogels), variations in temperature, small molecules (e.g., NO-responsive hydrogels), or light.

In these examples, the materials typically exhibit a single response to a single type of signal. Living systems, in contrast, are capable of responding selectively to many signals (both chemical and physical), and providing unique responses to each signal. Living systems also exhibit remarkably amplified responses to an applied signal. Most responsive materials that are currently available cannot behave with such sensitivity and specificity.

One or more of the following documents may be useful in understanding one or more embodiments of the invention. Inclusion of a document herein is not an admission that it is prior art or that it adversely affects the patentability of any claim of this application. The documents are incorporated by reference as if rewritten herein. Where this specification differs from one or more of the cited documents, this specification controls. Documents of interest include Polaske, et al., *Org. Let.* 2010, 12 (21), 4944-47; McGrath, D. V., *Molec. Pharm.* 2005, 2(4), 253-63; Li, et al., *J. Am. Chem. Soc.* 2003, 125, 10516-17; Szalai, et al., *J. Am. Chem. Soc.* 2003, 125, 15688-89; Knoll, et al., *Adv. Mater.* 2010, 22, 3361-65; Coulembier, et al., *Macromol.*, 2010, 43, 572-74; Ortiz, et al., *J. Org. Chem.* 2010, 75, 6154-62; Lin, et al., *Chem. Commun.* 2009, 803-05; de Montigny, et al., *Anal. Chem.* 1987, 59, 1096-1101; Benson, et al., *Proc. Nat. Acad. Sci. USA*, 1975, 72(2), 619-22; Zhang, et al., *Macromol.*, 2007, 40, 4154-58; Szali, et al., *Tetrahedron*, 2004, 60, 7261-7266; U.S. Pat. Nos. 4,734,481 and 4,820,829, to Steinmann; U.S. Pat. No. 7,625,764, to Stayton, et al.; International Patent Application Publication No. WO2008/053479, to Shabat, et al.; Tsuda, et al., *J. Polymer Sci.*, 1997, 35, 77-89; Shabat, et al., *Chem. Eur. J.*, 2004, 10, 2626-34; DeWit, et al., *J. Am. Chem. Soc.*, 2009, 131, 18327-34; Esser-Kahn, et al., *J. Am. Chem. Soc.* 2010, 132, 10266-68; Knoll, et al., *Adv. Mater.* 2010, 22, 3361-3365; Ortiz, et al., *J. Org. Chem.*, 2010, 75, 6154-62; Lahann, J.; Langer, R. *MRS Bulletin* 2005, 30, 185-188; Mendes, P. M. *Chem. Soc. Rev.* 2008, 37, 2512-2529; Tokarev, I.; Minko, S. *Soft Matter.* 2009, 5, 511-524; Yerushalmi, R.; Scherz, A.; van der Boom, M. E.; Kraatz, H.-B. *J. Mater. Chem.* 2005, 15, 4480-1487. Stuart, M. A. C.; et al. *Nat. Mater.* 2010, 9, 101-113. Yoshida, M.; Lahann, J. *ACS Nano* 2008, 2, 1101-1107; Grzybowski, B. A.; Whitesides, G. M. *Science* 2002, 296, 718-721. Zhang, et al., *Nano Lett*, 2009, 9, 3663-3667; Mallouk, T. E.; Sen, A. *Sci. Am.* 2009, 300, 72-77. (d) Ismagilov, R. F.; Schwartz, A.; Bowden, N.; Whitesides, G. M. *Angew. Chem. Int. Ed.* 2001, 41, 652-654. (e) Mano, N.; Heller, A. *J. Am. Chem. Soc.*, 2005, 127, 11574-11575. (f) Pantarotto, D.; Browne, W. R.; Feringa, B. L. *Chem. Commun.*, 2008, 1533-1535; Whites, S. R., et al., *Nature* 2001, 409, 794-797; Urban, M. W. *Prog. Polym. Sci.* 2009, 34, 679-687. (c) Murphy, E. B.; Wudl, F. *Prog. Polym. Sci.* 2010, 35, 223-251; Wool, R. P. *Soft Matter.* 2008, 4, 400-418; Kim, J.; Yoon, J.; Hayward, R. C. *Nature Mat.* 2009, 9, 159-164; Motornov, M., et al., *Langmuir* 2003, 19, 8077-8085; Rogers, C. *Sci. Am.* 1995, 154-157; Hu, J., Shape Memory Polymers and Textiles, CRC Press, 2007; Bellin, I.; Kelch, S.; Langer, R.; Lendlein, A. *Proc. Natl. Acad. Sci., U.S.A.* 2006, 103, 18043-18047; Lendlein, A.; Langer, R. *Science* 2002, 296, 1673-1676; Lendlein, A.; Jiang, H.; Jünger, O.; Langer, R. *Nature* 2005, 434, 879-882; Jaguar-Grodzinski, J. *Polym. Adv. Technol.* 2010, 21, 27-47; Schild, H. G. *Prog. Polym. Sci.* 1992, 17, 163-249; Chen, J.; McNeil, A. J. *J. Am. Chem. Soc.* 2008, 130, 16496-16497; Yu, Y.; Nakano, M.; Ikeda, T. *Nature* 2003, 425, 145; Li, M.-H.; Keller, P.; Li, B.; Wang, X.; Brunet, M. *Adv. Mater.* 2003, 15, 569-572; Liu, J., et al., *Adv. Mater.* 2008, 20, 2508-2511; Qiu, Z.; Yu, H.; Li, J.; Wang, Y.; Zhang, Y. *Chem. Commun.* 2009, 3342-3344; Krieg, E.; Shirman, E.; Weissman, H.; Shimoni, E.; Wolf, S. G.; Pinkas, I.; Rybtchinski, B. *J. Am. Chem. Soc.* 2009, 131, 14365-14373; Komatsu, H., et al., *J. Am. Chem. Soc.* 2009, 131, 5580-5585; Ito, H.; Willson, C. G. *Polym. Eng. Sci.* 1983, 23, 1012-1018; Aso, C.; Tagami, S.; Kunitake, T. *J. Polym. Sci., Part A: Polym. Chem.* 1969, 7, 497-511; Ito, H. *J. Polym. Sci., Part A: Polym. Chem.* 2003, 41, 3863-3870; Köstler, S.; Zechner, B.; Trathnigg, B.; Fasl, H.; Kern, W.; Ribitsch, V. *J. Polym. Sci., Part A: Polym. Chem.* 2009, 47, 1499-1509; Tsuda, M.; Hata, M.; Nishida, R.; Oikawa, S. *J. Photopolym. Sci. Technol.* 1993, 6, 491-494; MacDonald, S. A.; Willson, C. G.; Fréchet, J. M. J. *Acc. Chem. Res.* 1994, 27, 151-158; Amir, R. J., et al., *Angew. Chem. Int. Ed.* 2003, 42, 4494-4499; de Groot, F. M. H.; Albrecht, C.; Koekkoek, R.; Beusker, P. H.; Scheeren, H. W. *Angew. Chem. Int. Ed.* 2003, 42, 4490-4494; Sagi, A.; Weinstain, R.; Karton, N.; Shabat, D. *J. Am. Chem. Soc.* 2008, 130, 5434-5435; Weinstain, R.; Baran, P. S.; Shabat, D. *Bioconjugate. Chem.* 2009, 20, 1783-1791; DeWitt, M. A.; Gillies, E. R. *J. Am. Chem. Soc.* 2009, 131, 18327-18334; Sella, E.; Lubelski, A.; Klafter, J.; Shabat, D. *J. Am. Chem. Soc.* 2010, 132, 3945-3952; Nakayama, K.; Uoto, K.; Higashi, K.; Soga, T.; Kusama, T. *Chem. Pharm. Bull.* 1992, 40, 1718-1720; Hayakawa, Y.; Kato, H.; Uchiyama, M.; Kajino, H.;

Noyori, R. *J. Org. Chem.* 1986, 51, 2400-2402; and Corey, E. J.; Venkateswarlu, A. *J. Am. Chem. Soc.* 1972, 94, 6190.

BRIEF SUMMARY OF THE INVENTION

We describe a new class of plastics that are both sensitive and specific in their responses. These plastics comprise polymers that depolymerize autonomously in response to specific signals. In preferred embodiments the signals are chemical signals. Typically plastics of the invention are poly(phthalaldehydes), but other polymers are also included.

The polymers according to the claimed invention differ in their end-capping groups and response profiles. Plastics composed of claimed polymers may be self-powered (i.e., once the depolymerization is initiated, no further reagents are needed), and are capable of changing shape in a signal-dependent manner. This allows a composite plastic to be formed of the inventive polymer and a standard polymer that does not have the responsive properties of the inventive polymers. Therefore, that plastic may have two shapes; one shape formed by the inventive polymer and the nonresponsive polymer, and one shaped formed when the responsive, inventive polymer has been completely or partially depolymerized.

In a further embodiment the polymers may only require a modicum of power to depolymerize, allowing a user to control depolymerization by carefully moderating temperature or by adding a convenient heat source; for example, by heating a solvent to boiling or by rubbing between a user's hands an object comprising a polymer of the invention.

Other embodiments of the invention may include articles made from or including the inventive polymers. Further embodiments may include methods of making the inventive polymers.

BRIEF DESCRIPTION OF THE FIGURES

FIG. 5 shows selected examples of polymers according to embodiments of the invention.

FIG. 6 shows a method of synthesis for a poly(phthalaldehyde) with a linker according to an embodiment of the invention.

FIG. 14 shows synthesis routes for a two-methoxy poly(ether).

FIG. 15 shows polymers cross-linked by depolymerizable poly(ethers).

DETAILED DESCRIPTION OF THE INVENTION

I. Signal-Responsive Polymers and their Uses

Figure 1:
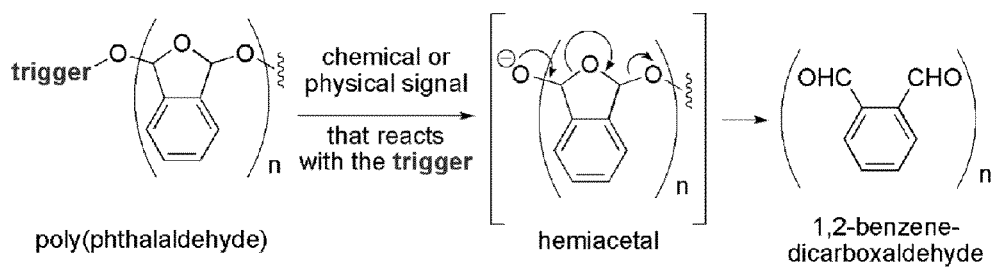
FIG. 1 shows an example of a signal-responsive polymer that depolymerizes selectively in the presence of a specific environmental signal.

It should be noted that throughout this disclosure the terms "end-cap," "trigger," and "triggering group" are used interchangeably and are separate from "capping group." Various principles and advantages of the invention may be shown using the example of poly(phthalaldehyde). Of course, it will be understood that embodiments of the invention are not limited to poly(phthalaldehyde) or its derivatives. Those of skill in the art will recognize that the ceiling temperature of poly(phthalaldehyde) without an end-capping group (i.e., the hemiacetal form shown in FIG. 1) is −40° C. In the presence of an end-capping group (e.g., acetate), however, the polymer is stable up to 180° C.

Our responsive polymers take advantage of this difference in stability. The literature teaches how to prepare poly(phthalaldehydes) with capping groups and end-caps that are unresponsive to applied chemicals. These capping groups and end-caps are purposely made to be stable so that the resulting polymers are stable. Poly(phthalaldehydes) are made to depolymerize in response to acid by acid-catalyzed degradation of the acetal linkages in the polymer. It has been shown that a minor reaction in this acid-catalyzed degradation is cleavage of the end-cap from these known polymers. Acid, however, is a general chemical signal, and the methods for preparing poly(phthalaldehydes) that are sensitive to acid do not obviously lead to methods that enable poly(phthalaldehydes) to depolymerize in response to specific applied signals other than acid. Moreover, because acid-catalyzed cleavage of the end-cap is only a minor reaction, the methods for end-capping poly(phthalaldehydes) do not teach how to end-cap with functionality that cleaves in response to a specific applied signal only at the end-cap, rather than at random locations along the polymer backbone.

Herein, we describe synthetic methods for adding end-caps to poly(aldehydes) and poly(ethers) that enable the polymers to depolymerize in response to specific applied signals, including, but not limited to, fluoride, palladium(0), hydrogen peroxide, and enzymes. The development of these synthetic methods required substantial invention, including: (1) the development of reagents and synthetic protocols that enable end-capping of poly(phthalaldehyde) and other poly(aldehydes) with end-caps that are stable, yet highly reactive when exposed to a specific signal; (2) the development of a linker that connects the polymers with the reactive end-cap (this linker is critical for adding certain types of end-caps, such as substrates for enzymes, to the polymers); (3) the development of a second synthetic method for incorporating these linkers into poly(phthalaldehyde) and other poly(aldehydes); (4) the discovery that benzylic ethers can be released quickly in response to an applied signal under neutral conditions when electron donating groups are added to the aromatic ring; and (5) the development of synthetic methods that take advantage of the discovery in (4) to prepare poly(ethers) that are capable of depolymerizing under neutral conditions.

Our methods enable the preparation of polymers that contain 2 to 10,000 repeating units in preferred embodiments with a most preferred length of 1000 repeating units. Those skilled in the art will recognize that even longer polymers are possible using methods taught herein. Depolymerizable poly(ether) and poly(carbamate) oligomers of 2 to 17 repeating units have been reported, but these reports do not teach how to prepare polymers (rather than oligomers) of substantial length. The length of the polymer is important for two reasons: (1) longer polymers give a larger amplified response when depolymerized as a result of an applied signal (for example, for diagnostic applications, an amplification factor of 17 from a 17-unit long oligomer increases the sensitivity of an assay only 17 times, whereas a 1000-unit long polymer would increase the sensitivity by 1000 times); and (2) longer polymers are more easily manipulated to make films, coatings, plastics, and other materials. Moreover, the methods for adding end-caps to reported oligomers are not transferable to other polymers, such as poly(phthalaldehyde) and other poly(aldehydes).

As we show herein, unique synthetic methods and chemical strategies must be employed to add responsive end-caps to poly(phthalaldehyde), other poly(aldehydes), as well as to poly(ethers). In addition, the reports on poly(ethers) teach only how to degrade the oligomers under basic conditions in organic solvent, whereas we describe a solution for depolymerizing poly(ethers) in a variety of solvents, including water, and in solutions that are neutral, basic, or acidic.

A further point that distinguishes our depolymerizable poly(ethers) from previous reports is the stability of our poly(ethers). Our invention provides poly(ethers) that are stable in the presence of acid, base, heat, or light, whereas known poly(phthalaldehydes) degrade under these conditions. Likewise, known depolymerizable poly(carbamate) oligomers degrade in the presence of acidic and basic water, or heat. Our poly(ethers), in contrast, show no signs of degradation in the absence of the specific applied signal when stored in water for more than 1 month.

We have prepared various derivatives of poly(phthalaldehyde), each with a different end-capping group—or "trigger"—that is cleaved from the poly(phthalaldehyde) derivative in response to certain chemical or physical signals in the environment. Of course, those skilled in the art will, with the benefit of this disclosure, recognize that changes in the temperature-dependence of other polymers through addition of end-capping groups will permit those polymers to also be used in embodiments of the invention. Cleaving the trigger results in depolymerization of the polymer. We believe that the synthesis and use of poly(phthalaldehydes), as well as other poly(aldehydes), poly(acetals), poly(alkyl sulfones), and poly(ethers) that depolymerize in response to specific chemical signals (rather than non-specific signals such as acid or base) is a new technology.

Depolymerization may be made to occur in air, in liquid solution, or both, depending on desired properties and uses for the polymer. A liquid solution may be, for example, but is not limited to, water (distilled, deionized, buffered, ocean, stream, lake, and any natural source of water), organic solvents (including, but not limited to tetrahydrofuran, ethyl acetate, dichloromethane), oils, gels, and biological fluids (including, but not limited to tears, saliva, sputum, sweat, blood, plasma, serum, urine, and cerebrospinal fluid).

Although poly(phthalaldehydes) are known to depolymerize in the presence of acid, acid is a non-specific chemical signal. Furthermore, the depolymerization is by random cleavage of a polymer backbone, not solely by cleavage of an end-cap. In contrast, in embodiments of the invention the exposure to a signal causes only the end-cap to cleave, which then results in the depolymerization of the entire polymer.

Figure 4:
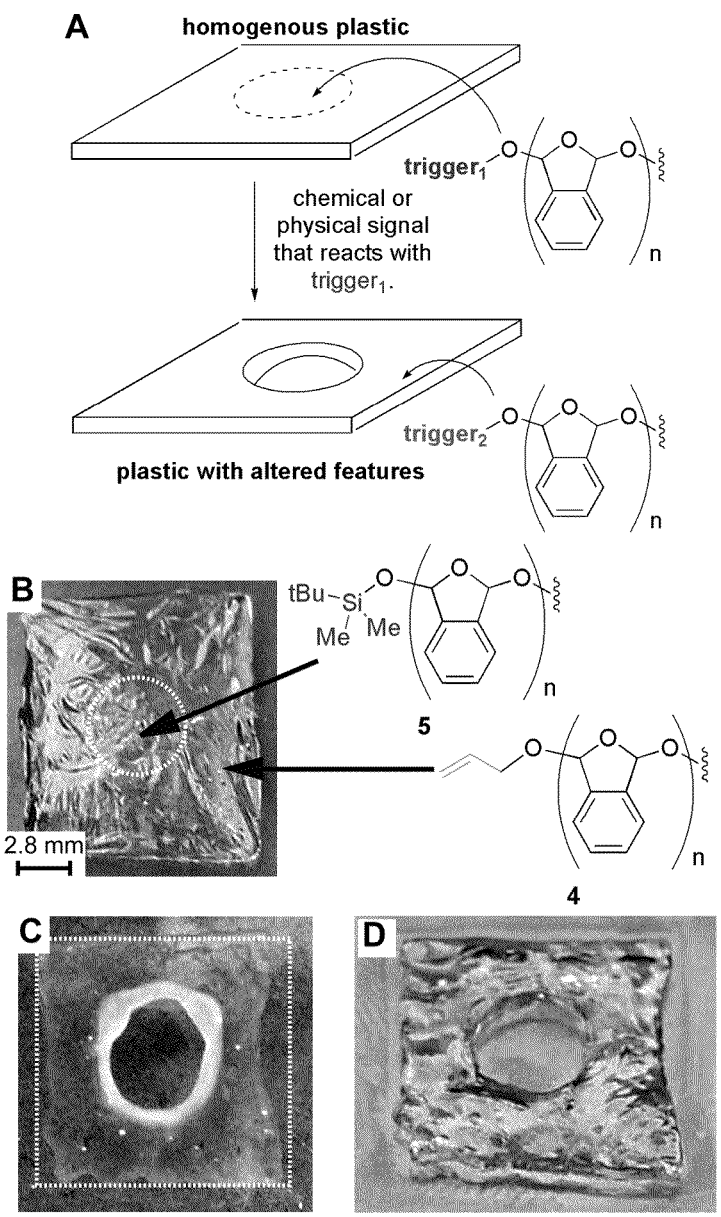
FIG. 4 shows an example of at least one material incorporating an embodiment of the invention.

Various embodiments include but are not limited to substituted poly(phthalaldehydes), substituted and unsubstituted poly(aldehydes), poly(acetals), poly(ethers), poly(esters), and poly(alkyl sulfones). As shown in FIG. 4, copolymers may also be used. As will be discussed with more specificity following the discussion of the various chemical structures that are suitable as polymers of the invention, each polymer should include an end-cap, and may further include a linker between the end-cap and the polymer and/or other modifications.

Although embodiments described herein have been described to this point as polymers, it will be understood by those skilled in the art that copolymers may be used. These may include for example but are not limited to block copolymers, statistical copolymers, periodic copolymers, and alternating copolymers.

Polymers used in the invention may be of any desirable length. When "n" is the length of the polymer in units, preferred polymers may have n between 2 to 10,000, n between 2 and 5000, n between 2 to 1000, n between 2 to 500, n between 2 to 400, n between 2 to 300, n between 2 to 200, n between 2 to 100, n between 2 to 50, and n between 2 and 10. In further embodiments the polymers have n between to 50 and 10,000, n between 50 and 5000, n between 50 and 1000, n between 50 and 500, n between 50 and 400, n between 50 and 300, n between 50 and 200, n between 50 and 100, and n between 20 and 50. In additional embodiments the polymers have n between to 100 and 10,000, n between 100 and 5000, n between 100 and 1000, n between 100 and 500, n between 100 and 400, n between 100 and 300, and n between 100 and 200. In even more embodiments the polymers have n between to 200 and 10,000, n between 200 and 5000, n between 100 and 1000, n between 200 and 500, n between 200 and 400, and n between 200 and 300. In yet still further embodiments n is at least 2, at least 10, at least 50, at least 100, at least 1000, or at least 10,000. These ranges may be applied to any of the uses of "n" in the disclosure presented here. As those of skill in the art will recognize, the ability to create long polymer chains is significant because such polymers may be made into plastics, films, and other macroscopic material.

Polymers of the invention may find many beneficial uses. For example, one might envision an embodiment in which a contact lens is caused to depolymerize in a mixture of tears and an eyedrop-like additive. In a further embodiment, a delivery system for a medicament could be developed that would depolymerize upon exposure to blood or cerebrospinal fluid. Cryptographic applications in which depolymerization would reconfigure an article and provide useful information could also be envisaged. Sensors might also be envisioned, where depolymerization is indicative of the presence of a chemical signal that reacts with the end-cap. Specialized optics might also be developed where, for example, a lens comprising an inventive polymer changes shape or polarization upon exposure to its trigger.

Yet still further embodiments of the invention may provide reversible adhesives in which the polymer serves as an adhesive, but then can be depolymerized and vaporized by exposure to a signal to remove the adhesive without damaging or adversely affecting the materials that were adhered together. Another embodiment provides materials that disappear when exposed to a signal; these could be used, for example, for covert operations, as casings for electronic memory components, as temporary packaging for sensitive electronic components, as surgical devices (e.g., stents, staples, sutures, shunts, and other items that can be caused to disappear by application of either infrared light, or a certain chemical signal applied via injection or through an ingestible tablet or drink), to create flushable plastics for applications in new types of hygiene products, to create plastics that are recycled easily and with limited input of energy by reversion to monomers in response to a specific chemical signal, or in plastic bags (or other types of plastics) that depolymerize when they contact the ocean or some other locality.

Another embodiment provides a method of amplification of signal for applications in detection; depolymerization would be indicative of the presence of the signal. A further embodiment provides a method of amplification in which the monomers that arise from depolymerization provide a readout that indicates the presence of the initial signal; these readouts include, but are not limited to, colored monomers, fluorescent monomers, monomers that are diamagnetic or paramagnetic (whereas the polymer would exhibit much higher levels of paramagnetism than the monomers), monomers that interact with another medium to form an observable readout (for example, monomers that cause another medium to become colored or fluorescent, or to polymerize or form a gel, or that induce movement of objects in solution). A further embodiment provides an 'on' "switch" in microfluidic devices that allows fluid to pass through a certain location in the presence of the specific chemical signal. Another embodiment provides a capsule or film for releasing components (e.g., dye for amplification of signal for applications in detection, or for releasing reagents that effect a chemical transformation). A further embodiment provides a coating for electronics. This may be, for example, but is not limited to a responsive coating on an electrode that blocks the transfer of current through solution to another electrode unless the signal is in solution and causes the polymer to depolymerize.

In further embodiments one might envision an article that comprises a plurality of polymers that are similar but for their triggers. That would provide a user with multiple options for alteration of the article, since he would have the ability to subject it to one or more triggers depending on the desired result. We expect that macroscopic materials composed of these types of responsive polymers will find applications in settings where life-like response characteristics (i.e., changing shape in response to environmental signals) are more important than long-term structural stability. We also anticipate that the modular construction strategy for these responsive materials will facilitate the fabrication of materials that respond to a variety of signals, including enzymes, small organic and inorganic molecules, metals, heat, and ultraviolet, visible, and/or infrared light. Applications include but are not limited to:

Grocery bags and other plastics that disappear when they contact microorganisms in the ocean (or other signals in other environments).

Materials that reconfigure themselves to accommodate a new environment or application.

Amplification for trace-level detection of biomarkers of disease.

Changing wetting properties of paper, or other type of material. The property could be used as a stimuli-responsive meter for controlling flow rate in paper-based diagnostic devices.

Stimuli-responsive coatings.

Stimuli-responsive capsules for the immediate release of contents (e.g., drug delivery).

Reversible adhesives.

New types of "single-use", low energy plastics that are easily recycled into monomers without melting (i.e., without applying energy in the form of heat).

EVAP-materials: that is, materials that respond to external signals and disappear. These types of plastics could be useful for covert military applications, diapers, hygiene products, etc. One version of the polymers will depolymerize in the presence of hydrogen peroxide, which is present in urine.

A simple example of how a material incorporating at least one polymer of the invention might function is shown in FIG. 4. That Figure shows a homogenous plastic film that reveals a circular hole when exposed to fluoride. FIG. 4(A) shows an embodiment of signal-responsive plastics. Trigger$_1$ responds to one chemical signal, while trigger$_2$ either is non-responsive, or is capable of responding to a different signal. When trigger$_1$ responds, the pendant poly(phthalaldehyde) polymers depolymerize to reveal a new pattern in the original plastic. FIG. 4(B) shows a film consisting of polymer 5 patterned in a circular pattern in a film of polymer 4. The dotted white line indicates the approximate position of polymer 5. FIG. 4(C) shows a photograph of the film (still in solution) 7 minutes after exposure to fluoride. The white dotted box indicates the approximate edges of the film. FIG. 4(D) shows a photograph of the film after 15 minutes exposure to fluoride and after washing the film with diethyl ether. The photographs were enhanced in Adobe® Photoshop® using the "auto levels" function.

Although many embodiments are discussed in terms of poly(phthalaldehydes), it will be understood that other polymers are also suitable candidates for addition of triggers that may create polymers of the invention. Additional non-limiting examples of polymers suitable for use in the invention are presented in FIG. 5 and discussed in the subsections below. These polymers include poly(ethers), poly(aldehydes), poly(acetals), poly(esters), and poly(alkyl sulfones) that are made to depolymerize in response to a specific signal. The elements used to enable this type of depolymerization response includes a polymer and an end-cap, and sometimes a linker. In the case of poly(esters), poly(ethers), and poly(alkyl sulfones), the end-cap can be located at either terminus of the polymer, at both termini simultaneously, or at each repeating unit within the polymer. Combinations of these locations are possible as well, including end-caps at each repeating unit and at one or both termini, and end-caps at a fraction of the repeating units and at one or both termini. Each type of polymer (i.e., poly(ethers), poly(aldehydes), poly(acetals), poly(esters), and poly(alkyl sulfones)) have different physical and mechanical properties, and therefore each type of polymer will be suited to a particular application. For example, poly(ethers) are insensitive to mild acid and base, and do not hydrolyze readily in water, and therefore, this type of polymer will be useful for applications that require long-term stability, such as coatings that are responsive to specific signals. An example of this type of coating application is a corrosion-indicator coating that senses one or more chemical indicators of corrosion, and depolymerizes to reveal colored or fluorescent molecules.

II. Triggering Groups

Each polymer of the invention will include a triggering group that defines the stimulus that will initiate depolymerization. Selection of these triggering groups may be governed, for example, by factors including but not limited to the desired physical or chemical signal for depolymerization. Possible triggering groups are listed below. For each triggering group the signal that will be recognized by the triggering group and lead to depolymerization is included in parentheses following the triggering group. They may include, for example, but are not limited to allyl carbonate (palladium(0)), allyl ether (palladium(0)), allyl carbamate (palladium(0)), tert-butyldimethylsilyl ether (fluoride), triethylsilyl ether (fluoride), other silyl ethers (fluoride), vinyl ether (mercury), ortho- or para-nitrobenzyl ether (UV light), ortho- or para-nitrobenzyl carbonate (UV light), ortho- or para-nitrobenzyl carbamate (UV light), aryl boronate (hydrogen peroxide), and aryl boronic acid (hydrogen peroxide). Additional triggers can include substrates for enzymes (including, but not limited to substrates for proteases, glycosidases, glucosidases, beta lactamases, and substrates for any other enzyme that cleaves a bond). An exemplary polymer that contains a triggering group that cleaves from the polymer when exposed to UV light is:

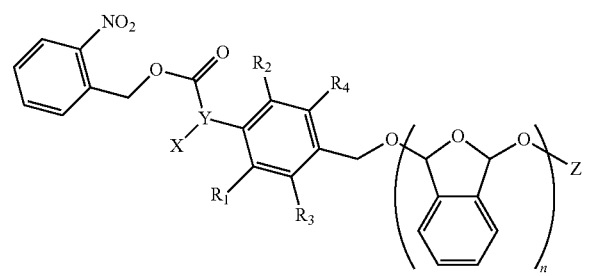

Y=oxygen, nitrogen, or sulfur
X=C1-C30 alkyl, including $CH_3$—, when Y is nitrogen
Z=ethers (e.g., $CH_3$—), esters (e.g., $CH_3CO$—), carbonates (e.g., $CH_3OCO$—), or carbamates (e.g., $CH_3NHCO$—).
$R_1$, $R_2$, $R_3$, and $R_4$ are independently selected and may be H, or OMe, or O-Alkyl, or O-Aryl.

III. Capping Group

In addition to the polymer unit and the triggering group, embodiments of the invention have a capping group at the terminus of the polymer remote from the triggering group. Although not so critical as the triggering group, the capping group may still be selected to give beneficial effects to the overall polymer. For example, certain capping groups may be selected to (i) increase the yields of the polymerization reaction; (ii) increase the rate of the polymerization reaction; (iii) increase the length of the polymer; (iv) increase or decrease the polydispersity of the polymer; (v) increase the stability of the polymer to minimize non-specific depolymerization; (vi) serve as a chemical handle for attaching the polymer to surfaces or other reagents; and (vii) continue the depolymerization process of neighboring polymers by releasing a reagent that cleaves the trigger of neighboring polymers.

Capping groups may include, for example, but are not limited to alkyl, C1-C30 branched or linear alkyl, C1-C30 branched or linear alkyl, C2-C6 branched or linear alkyl, C1-C6 branched or linear alkyl, and may be appended to the polymer using an alcohol, an amine, a thiol, alkyl grignard reagents, aryl grignard reagents, a lithium salt, a copper salt, a sodium salt, a potassium salt, a cesium salt, a magnesium salt, a lithium alkoxide, a sodium alkoxide, a potassium alkoxide, a cesium alkoxide, a magnesium alkoxide, a copper alkoxide, and an alkyl hydroperoxide.

IV. Linkers

Some polymers of the invention include a linker between the polymer and the end-cap. Inclusion of a linker may have a number of beneficial effects, including allowing an artisan to incorporate a variety of end-caps during the polymerization reaction. These end-caps may include substrates for enzymes. The enzymes may be, for examples, proteases or glycosidases.

When the end-cap is cleaved in response to a specific chemical signal, the linker releases the polymer by forming either quinone methide or azaquinone methide, including both ortho- and para-quinone methide and ortho- and para-azaquinone methide derivatives. The linkers can possess a variety of substituents to increase or decrease the rate of release of the polymer, or to provide another function, such as releasing two or more polymers from a single linker. Which of those compounds is formed is determined by whether the end-cap (X, as shown in the final paragraph of Section III, above) is connected to the linker through an oxygen atom or a nitrogen atom. These linkers are most easily added to a polymer of the invention by the method shown in FIG. 6.

An exemplary linker is shown below:

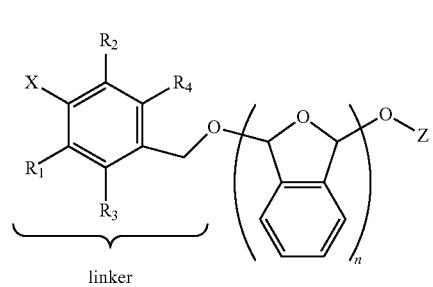

linker

In this example, X is a triggering group that cleaves in the presence of a specific chemical signal. Examples include but are not limited to $R_3SiO$-aryl, $(RO)_2B$-aryl, $CH_2CHCH_2OCO_2$-aryl, polysaccharide-O-aryl, and peptide NH-aryl, where aryl is the aromatic ring that is connected to X. The aryl group in the linker can include, but is not limited to, substituted benzene derivatives, substituted pyridine derivatives, substituted naphthalene derivatives, substituted anthracene derivatives, and other aromatic and heteroaromatic groups. Z is a capping group. $R_1$, $R_2$, $R_3$ and $R_4$ are independently selected and may be hydrogen, OMe, O-alkyl, O-aryl, NH-alkyl, NH-aryl, N(alkyl)$_2$, N(aryl)$_2$, $CO_2R$ (where R is alkyl, aryl, hydrogen, and substituted nitrogens). It should be noted that throughout this disclosure the terms "end-cap," "trigger," and "triggering group" are used interchangeably and are separate from "capping group."

V. Modification Through Other Conservative Substitutions

Additional modifications may be made, as desired, to impart further desired properties to polymers prepared according to the invention. These modifications may be made through conservative substitutions. For example, the poly (phthalaldehydes) described herein may be substituted to have one or more effects including but not limited to (a) extending the conjugation to make the resulting monomers colored or fluorescent; (b) increasing hydrophilicity; (c) increasing hydrophobicity; (d) increasing non-covalent interactions with surfaces (for adhesives applications); (e) attaching the polymer covalently to a surface; (f) decreasing crystallinity and other physical properties to increase the ease with which the polymer can be dissolved, molded, and otherwise manipulated; and (g) increasing or decreasing the rate of depolymerization by increasing or decreasing strain or charge repulsion, for example.

VI. Examples

Various examples of trigger-responsive polymers and methods of their synthesis are described below. One of skill in the art will understand that although a specific method of making a polymer may be indicated herein, use of that specific method of synthesis is not a prerequisite of satisfying any or all limitations of a claim unless that claim specifically requires a given synthesis method.

A. Poly(Phthalaldehydes)

1. Compounds

Poly(phthalaldehydes) of the invention may have the following formula, where X is a substrate that responds to a specific chemical signal:

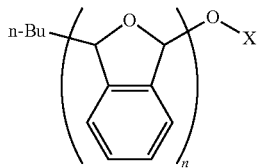

Figure 2:
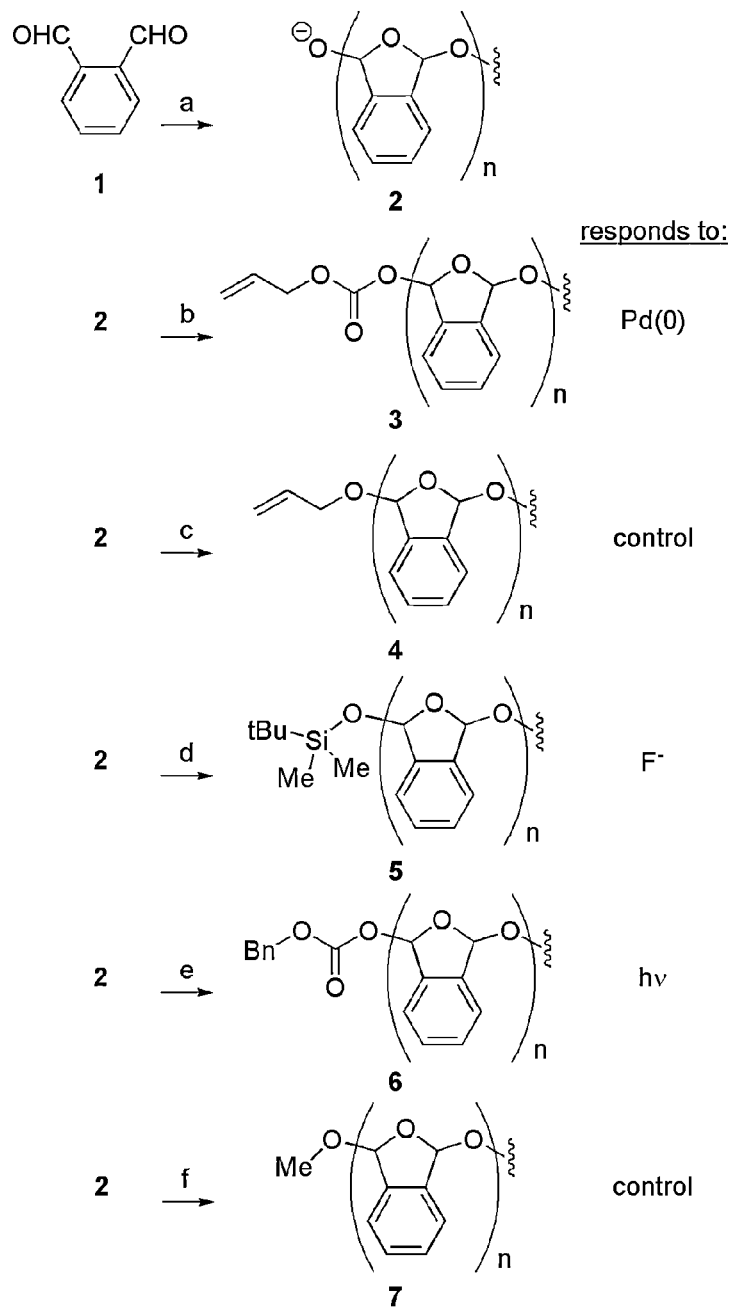
FIG. 2 shows examples of the synthesis of multiple polymers of the invention, each with a different end-capping group that is responsive to a different signal.
Figure 3:
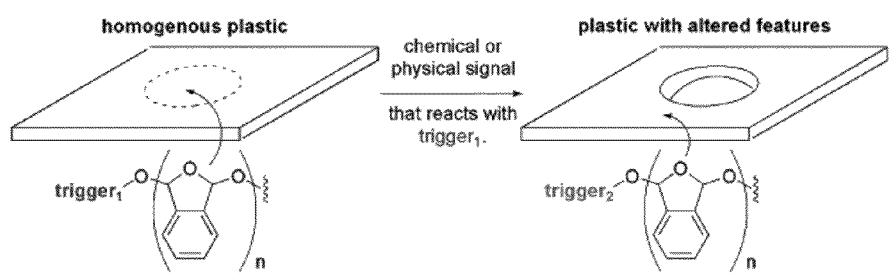
FIG. 3 shows an example of an article of manufacture that may be created from signal-responsive polymers of the invention. The figure also shows how the structure of the article may be changed in the presence of the signal to which one of the two component polymers responds.

Examples of this embodiment and their synthesis are given in compounds 3, 5, 6, and 7 in FIG. 2.

Poly(phthalaldehydes) according to the invention may also include a linker, as discussed above. Those poly(phthalaldehydes) may have the following formula, where X is a functionality that cleaves in the presence of a specific chemical signal:

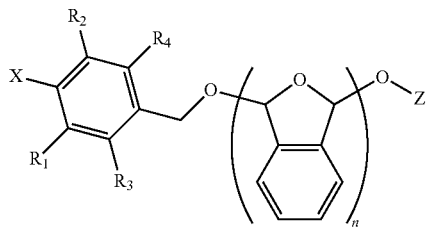

In this embodiment, X may be, for example, $R_3SiO-$, $(RO)_2B-$, $CH_2CHCH_2OCO_2-$, monosaccharide-O— (i.e., a single sugar unit, including both natural and unnatural sugars; an example is a beta-D-glucuronic acid unit, which is cleaved at the anomeric position by the enzyme beta-D-glucuronidase), polysaccharide-O— (i.e., multiple sugar units linked together, both as linear and branched polysaccharides, including, but limited to glycosaminoglycans; an example is starch, which is cleaved at the anomeric position by amylase), or peptide-NH— (i.e., a specific peptide sequence comprised of natural amino acids, unnatural amino acids, or both, and including peptidomimetics that are recognized as substrates by specific proteases; an example peptide is alanine-phenylalanine, which is cleaved by chymotrypsin at the carboxy terminus of the peptide). Z is a functionality arising from addition of an anhydride (e.g., $Ac_2O$), isocyanate (e.g., PhNCO), alkylating reagent (e.g., methyl iodide), acid chloride (e.g., AcCl), chloroformate (e.g., $ClCO_2Ph$), or acid fluoride (e.g., AcF) to the end of the polymer. Z, therefore, would be an ether (e.g., polymer-OMe), an ester (e.g., polymer-$OCOCH_3$), a carbamate (e.g., polymer-OCONHPh), or a carbonate (e.g., polymer-$OCO_2Ph$).

Z could also include functionality that releases more of the chemical signal that reacts with the end-cap. A non-limiting example of this type of functionality is shown below, although one skilled in the art would recognize that other combinations of X and Z are possible. In this specific example, X is an end-cap that is cleaved by fluoride (the signal) (an example of X in this case is triethylsilyl ether of the type $Et_3SiO$-linker-polymer-Z or $Et_3SiO$-polymer-Z), and Z is a carbamate that, upon depolymerization, is liberated from the polymer as carbon dioxide and an aniline derivative. Once released from the polymer, the aniline derivative will eject both of the geminal fluorine substituents via formation of azaquinone methide.

$R_1$, $R_2$, $R_3$, and $R_4$ are independently selected and may be, for example, hydrogen, OMe, O-alkyl (C1-C30 linear or branched), O-aryl, NH-alkyl (C1-C30 linear or branched), O-poly(ethylene glycol) (1-20 repeating units), NH-aryl, $N(alkyl)_2$, $N(aryl)_2$, $CO_2R$ (where are is alkyl, aryl, hydrogen, and substituted nitrogens). The aromatic unit of the linker can include, but is not limited to, substituted benzene derivatives, substituted pyridine derivatives, substituted naphthalene derivatives, substituted anthracene derivatives, and other aromatic and heteroaromatic groups. These compounds may be synthesized, for example, by the scheme shown in FIG. 6. Note that "alkyl" as used throughout this disclosure includes branched and straight-chain carbon and hydrogen compounds having between one and thirty carbon atoms, preferably between one and 15 carbon atoms, most preferably between one and 6 carbon atoms. "Aryl" as used herein includes branched and straight-chain carbon and hydrogen compounds including at least one double bound and having between one and thirty carbon atoms, preferably between one and 15 carbon atoms, most preferably between one and 6 carbon atoms.

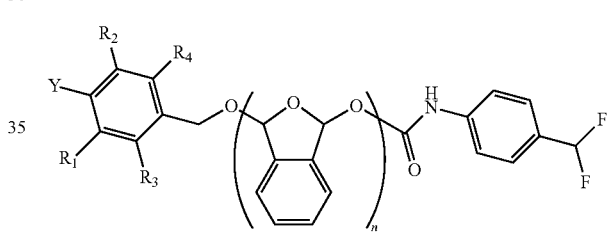

2. Synthesis a. General Provisions

Generally, synthesis of these compounds may be achieved by anionic polymerization at temperatures below −40° C. We use two general methods for preparing poly(phthalaldehydes), although it should be recognized that the specific reagents associated with these methods can be varied by one skilled in the art. The first method uses an alkyl lithium reagent as initiator (e.g., n-BuLi), which also serves as the capping group for the polymer. Typically, the triggering group is added to the other end of the polymer using an electrophilic reagent, such as triethylsilyl chloride, for example. The second method uses a catalyst and an alcohol as initiator. This alcohol can be the capping group, the triggering group, or the linker that contains the triggering group. In this method, the opposite end of the polymer is functionalized with either a capping group, triggering group, or linker that contains the triggering group. In both methods, after the polymer is initiated, it may be terminated with a nucleophilic substituent instead of an electrophilic substitutent (as described above), if the polymer is first activated with an electrophilic reagent such as triflic anhydride, followed by addition of a nucleophile (such as benzyl alcohol) that can be either a capping group, triggering group, or linker that contains the triggering group.

Method 1: As shown in FIG. 2, we synthesized poly(phthalaldehyde) using anionic polymerization conditions.

Responsive polymers 3, 5, and 6 were end-capped with either allyl chloroformate (3), tert-butyldimethylsilyl chloride (5), or benzyl chloroformate (6) to create polymers that respond to Pd(0), fluoride, or ultraviolet light (UV), respectively. We also prepared control polymers 4 and 7 to demonstrate that the triggers in polymers 3, 5, and 6 are responsible for the selective response characteristics. Synthesis materials and methods are discussed in detail below.

All reactions were performed in flame-dried glassware under a positive pressure of argon. Air- and moisture-sensitive liquids were transferred by syringe or stainless steel cannula. Organic solutions were concentrated by rotary evaporation (25-40 mmHg) at ambient temperature, unless otherwise noted.

Phthaldialdehyde was purchased from Alfa Aesar and was recrystallized from a mixture of dichloromethane and hexanes (5:2). The recrystallized material was dried by azeotropic removal of water with benzene in vacuo (3.5 mmHg, overnight). The recrystallized phthaldialdehyde was stored in a glove box for 2 days prior to use. All other chemicals were purchased from Aldrich and were used without further purification.

The molarity of solutions of n-butyllithium (n-BuLi) was determined by titration against diphenylacetic acid as an indicator (average of three determinations). Anhydrous tetrahydrofuran (THF) and dichloromethane were purified by the method of Pangborn et al, *Organometallics* 1996, 15, 1518-1520. Dry N,N-diisopropylethyl amine and pyridine were distilled over $CaH_2$ at 760 mmHg. Deionized water was purified with a Millipore-purification system (Barnstead EASYpure® II UV/UF). All reactions were carried out under an atmosphere of argon, which was passed through an Agilent oxygen trap BOT-4. The laser cutter employed was an Epilog laser (Epilog mini 8000).

b. Synthesis of Poly(Phthalaldehyde)

A solution of dry phthaldialdehyde (4.5 g, 34 mmol, 1.0 equiv) in THF (27 mL) was degassed by two freeze-pump-thaw cycles, and was sealed with a septum under an atmosphere of oxygen-free Ar. A 23° C. solution of n-BuLi in hexanes (1.6 M, 70 µL, 0.11 mmol, 0.0033 equiv) was injected quickly in one portion into the prepared monomer solution at 23° C. Immediately following the addition, the reaction mixture was cooled to −80° C. and was stirred at −80° C. for 13 days. The resulting light yellow solution of poly(phthalaldehyde) was stored at −80° C. and was used directly in the end-capping procedures described below.

c. Synthesis of Polymer 3

Allyl chloroformate (0.65 mL, 6.0 mmol, 0.18 equiv) (23° C.) was added in one portion to a freshly-prepared solution of poly(phthalaldehyde) (34 mmol of phthaldialdehyde monomer) in THF (27 mL) at −80° C. After 72 h of stirring at −80° C., polymer 3 was precipitated by the addition of 23° C. hexanes (50 mL) to the −80° C. reaction mixture. The solvent and polymer precipitate were transferred to a solid-phase washing vessel (see inset below) and the solvent was drained. The precipitated polymer was washed by adding solvent (described below) and then bubbling $N_2$ up through the solution at a vigorous rate.

After bubbling $N_2$ through the solution for 30 min, the solvent was drained. Polymer 3 was washed with diethyl ether (6×100 mL; 30 min per wash cycle) followed by methanol (2×100 mL; 30 min per wash cycle). The polymer was washed further using three cycles of the following sequence of solvents: ethyl acetate (100 mL; 30 min per wash) and diethyl ether (100 mL; 30 min per wash). After the last wash, the solvent was drained under vacuum (−40 mmHg), and the solid polymer was dried in vacuo for 24 h prior to use. Polymer 3 was obtained as a white solid (4.2 g, 94%). Mn: 19.9 KDa and Mw: 25.6 KDa. ($C_6D_6$): δ 7.58 (br m, 2H), 7.34 (br s, 2H) and 7.09-6.67 (br s, 2H). $^{13}C$ NMR($C_6D_6$): δ 139.66, 129.90, 123.75, 104.67, 104.25, 103.47.

d. Synthesis of Polymer 6

The preparation of polymer 6 is analogous to that described for polymer 3, except that benzyl chloroformate (0.86 mL, 6.0 mmol, 0.18 equiv) was used instead of allyl chloroformate. Polymer 6 was obtained as a white solid (3.2 g, 72%). Mn: 11.3 KDa and Mw: 14.1 KDa.

e. Synthesis of Polymer 4

A solution of allyl alcohol (0.48 mL, 7.0 mmol, 1.0 equiv) in N,N-diisopropylethylamine (1.2 mL, 7.0 mmol, 1.0 equiv) was stirred for 24 h at 23° C. Dichloromethane (3.0 mL) was added, and the reaction mixture was cooled to −78° C. Using a syringe, the cold solution was added dropwise to a −78° C. solution of trifluoromethanesulfonyl chloride (0.74 mL, 7.0 mmol, 1.0 equiv) in dichloromethane (3.0 mL). The reaction mixture was allowed to warm to 23° C. and was stirred for 24 h. The resulting solution of allyl triflate was used in the next reaction without purification.

A solution of allyl triflate in dichloromethane (1.2 M, 6.0 mL, 7.0 mmol, 0.21 equiv; described above) was added via cannula at −78° C. to a freshly-prepared solution of poly (phthalaldehyde) (34 mmol of phthaldialdehyde monomer) in THF (27 mL) at −80° C. The reaction mixture was stirred for 4 d at −80° C. Pyridine (1.5 mL, 19 mmol, 0.57 equiv) was added to the cold reaction mixture, and the resulting solution was stirred for an additional 30 min. Polymer 4 was precipitated by addition of 23° C. hexane (50 mL) to the cold reaction mixture, resulting in the formation of a white precipitate. The product solution was allowed to warm to 23° C., and then was transferred to a solid-phase washing vessel (see image above) and the solvent was drained.

The precipitated polymer was washed using the same process described above, but with the following solvents: diethyl ether (6×100 mL; 30 min per wash cycle) followed by methanol (2×100 mL; 30 min per wash cycle). Next, the polymer was washed further using three cycles of the following sequence of solvents: ethyl acetate (100 mL; 30 min per wash) and diethyl ether (100 mL; 30 min per wash). After the last wash cycle, the solvent was drained under vacuum (−40 mmHg), and the solid polymer was dried in vacuo for 24 h prior to use. Polymer 4 was obtained as a white solid (3.7 g, 83%). Mn: 21.7 KDa and Mw: 27.8 KDa.

f. Synthesis of Polymer 5

A solution of tert-butyldimethylsilyl chloride (TBSCl) (0.90 g, 6.0 mmol, 0.18 equiv) in THF (6.5 mL) was cooled to −78° C. and then was added in one portion via cannula to a freshly-prepared −80° C. solution of poly(phthalaldehyde) (34 mmol of phthaldialdehyde monomer) in THF (27 mL). The reaction mixture was stirred for 4 d at −80° C. Pyridine (1.5 mL, 19 mmol, 0.57 equiv, 23° C.) was added in one portion to the cold reaction mixture, and the resulting solution was stirred for an additional 30 min at −80° C. Polymer 5 was precipitated by the addition of hexane (50 mL, 23° C.) to the cold product solution. The heterogeneous product mixture was allowed to warm to 23° C., was transferred to a solid-phase washing vessel, and the solvent was drained.

The precipitated polymer was washed using the same process described above, but with the following solvents: diethyl ether (6×100 mL; 30 min per wash cycle) followed by methanol (2×100 mL; 30 min per wash cycle). Next, the polymer was washed further using three cycles of the following sequence of solvents: ethyl acetate (100 mL; 30 min per wash) and diethyl ether (100 mL; 30 min per wash). After the last wash cycle, the solvent was drained under vacuum (−40 mmHg), and the solid polymer was dried in vacuo for 24 h prior to use. Polymer 5 was obtained as a white solid (3.9 g, 86%). Mn: 15.3 KDa and Mw: 18.1 KDa.

g. Synthesis of Polymer 7

A solution of methyl trifluoromethanesulfonate (0.45 mL, 4.0 mmol, 0.18 equiv) in dichloromethane (5.0 mL) was cooled to −78° C. and was added in one portion via cannula to a freshly-prepared, −80° C. solution of poly(phthalaldehyde) (22 mmol of phthaldialdehyde monomer) in THF (12.5 mL). The reaction mixture was stirred for 4 d at −80° C. Pyridine (1.0 mL, 12 mmol, 0.36 equiv, 23° C.) was added to the cold reaction mixture in one portion, and the resulting solution was stirred for an additional 30 min at −80° C. Polymer 7 was precipitated by the addition of 23° C. hexane (50 mL) to the cold product solution. The heterogeneous product solution was allowed to warm to 23° C., was transferred to a solid-phase washing vessel and the solvent was drained. The precipitated polymer was using the same process described above, but with the following solvents: diethyl ether (6×100 mL; 30 min per wash cycle) followed by methanol (2×100 mL; 30 min per wash cycle). Next, the polymer was washed further using three cycles of the following sequence of solvents: ethyl acetate (100 mL; 30 min per wash) and diethyl ether (100 mL; 30 min per wash). After the last wash cycle, the solvent was drained under vacuum (~40 mmHg), and the solid polymer was dried in vacuo for 24 h prior to use. Polymer 7 was obtained as a white solid (2.5 g, 83%). Mn: 22.3 KDa and Mw: 24.4 KDa.

h. Synthesis of Poly(Phthalaldehyde) with Linker

Method 2: A representative synthesis of a poly(phthalaldehyde) with a linker is shown in FIG. 6. In a more specific embodiment, a solution of dry phthaldialdehyde (1.0 g, 7.5 mmol, 1.0 equiv) in THF (12 mL) was degassed by three freeze-pump-thaw cycles and was sealed with a septum under an atmosphere of oxygen-free Ar. Benzyl alcohol (1.5 µL, 0.015 mmol, 0.002 equiv) was added via syringe to the prepared monomer solution at 23° C. The solution was then brought to −78° C. in a $CO_2$/acetone bath for 1 minute before adding 1-tert-Butyl-2,2,4,4,4-pentakis(dimethylamino)-$2\Lambda^5$, $4\Lambda^5$-catenadi(phosphazene) ($P_2$-t-Bu, ~2.0M, 5 µL, 0.01 mmol, 0.001 equiv). After stirring at −78° C. for 2 hours, the polymerization was quenched by the addition of pyridine (180 µL, 2.2 mmol, 0.3 equiv) followed by tert-butyldimethylsilyl trifluoromethanesulfonate (170 µL, 0.75 mmol, 0.1 equiv).

The $CO_2$/acetone bath was allowed to warm slowly to 23° C. (~2 hours). The reaction mixture was poured into cold methanol (40 mL) and the polymer precipitated from solution was transferred to a solid-phase washing vessel and the solvent was drained. The precipitated polymer was washed with three cycles of the following of solvents: ethyl acetate (50 mL; 30 min per wash) and hexanes (50 mL; 30 min per wash). After the last wash cycle, the solvent was drained under vacuum, and the solid polymer was dried in vacuo for 24 hours. Poly(phthaldialdehyde) was obtained as a white solid (0.83 g, 83%). Mn: 32.4 KDa, Mw: 39.0 KDa, and PDI: 1.21.

3. Results a. Overall Results

Yields for the polymerization reactions using Method 1 are typically 76-94%. The number average molecular weights ($M_n$) for the polymers are dependent on reaction time, and range from 20 kDa (10 days reaction time) up to 33 kDa (13 days). Polymers with $M_n$ values of 20 kDa contain ca. 150 monomer units per polymer, whereas polymers with $M_n$ values of 33 kDa contain ca. 250 monomer units. Polydispersity indices for the polymers ranged from 1.11 for 20 kDa polymers up to 1.28 for 33 kDa polymers. When using Method 2, polymers with ~1000 repeating units are typically obtained, although variations in catalyst loading and reaction time provides access to shorter, or longer polymers, as needed.

Polymers 3-7 are stable for >22 h (i.e., they show essentially no signs of depolymerization) as 0.01 M solutions in tetrahydrofuran (THF) at 25° C. under an atmosphere of air (Table 1, Lines 1, 5, 8, 11, and 13). However, when polymer 3 is exposed to catalytic quantities of $Pd(PPh_3)_4$, the polymer depolymerizes within minutes in a dose-dependent manner (lines 2-4). The time-dependent $^1H$ NMR spectra in FIG. 2 reveal that this Pd(0)-triggered depolymerization is quantitative, rapid, and occurs without generation of byproducts; the only peaks apparent in the $^1H$ NMR spectrum correspond to the monomer, 1,2-benzenedicarboxaldehyde. Gel permeation chromatography (GPC) spectra revealed similar results.

TABLE 1

Solution-phase response rates of polymers 3-7 to various signals.[a]

| Line | Polymer | Signal | Equiv. of Signal[k] | Exposure Time (min) | Polymer Remaining (%)[l] |
|---|---|---|---|---|---|
| 1 | 3[b] | none | — | 930 | 95 |
| 2 | 3[b] | Pd(0)[g] | 0.40 | 5 | 0 |
| 3 | 3[b] | Pd(0)[g] | 0.08 | 5 | 10 |
| 4 | 3[b] | Pd(0)[g] | 0.01 | 5 | 89 |
| 5 | 4[c] | none | — | 960 | 99 |
| 6 | 4[c] | Pd(0)[g] | 0.5 | 320 | 95 |
| 7 | 4[c] | F[−h] | 0.5 | 25 | 97 |
| 8 | 5[d] | none | — | 1310 | 97 |
| 9 | 5[d] | F[−h] | 0 | 1080 | 96 |
| 10 | 5[d] | F[−i] | 0.5 | 1 | 0 |
| 11 | 6[e] | none | — | 1300 | 94 |
| 12 | 6[e] | hv[j] | — | 8.3 | 63 |
| 13 | 7[f] | none | — | 552 | 100 |
| 14 | 7[f] | hv[j] | — | 8.3 | 94 |

[a] All experiments were performed at 0.01 M concentrations of polymer in THF and at 25° C., except for when polymers were exposed to UV light; in these experiments, the polymer concentration was 0.0001 M in THF, and the temperature was held at ca. 0° C.
[b] $M_n$ = 19.9 kDa.
[c] $M_n$ = 21.7 kDa.
[d] $M_n$ = 15.3 kDa.
[e] $M_n$ = 11.8 kDa.
[f] $M_n$ = 22.3 kDa.
[g] $Pd(PPh_3)_4$.
[h] 1:2 THF-phosphate buffer (0.1 M, pH 7.1).
[i] 0.3 M TBAF in 1:2 THF-phosphate buffer (0.1 M, pH 7.1).
[j] Using a Intelli-Ray 600 shuttered UV metal halide lamp.
[k] Molar equivalents in relation to the polymer.
[l] Calculated from GPC data using the area (A) of peaks and the equation: $[A_{polymer}/(A_{polymer} + A_{monomer})] \times 100$.

The carbonate linkage between the polymer backbone and the end-capping group is critical to the response sensitivity of polymer 3. This result was demonstrated with control polymer 4, which also contains an allyl substituent in the end-capping group, but in this case, the allyl group is connected as an ether rather than as a carbonate. We found that polymer 4 showed negligible levels of depolymerization after exposure to 0.5 equivalents of $Pd(PPh_3)_4$ for >5 h; these results were expected based on the known relative reactivities of allyl ethers versus allyl carbonates.

Polymer 4 also is unaffected by the presence of fluoride, as would be expected; it shows negligible levels of depolymerization after 25 min (Line 7). Polymer 5 (0.01 M in THF), in contrast, depolymerizes completely in <1 min when exposed to 0.5 equivalents of fluoride. Similarly, polymer 6 depolymerizes in the presence of UV light, whereas control polymer 7 (methyl end-capping group) does not (Table 1, Lines 12 and 14). These experiments demonstrate the fine balance between stability of the polymer (as seen with control polymers 4 and 7) and sensitivity of response.

The responses of polymers 3-7 in the solid state (when the solid polymer is wet with ethyl acetate to deliver the signal) are attenuated in comparison to those in solution. This decrease in response rate likely is due to decreased accessibility of the triggers within the solid matrix. For example, when polymer 5 is cast as a 0.49 mm-thick film, it depolymerizes completely within 15 min of exposure to fluoride, whereas in solution, depolymerization occurs within 1 min as shown in FIG. 4.

b. Evaluating the Response of Polymer 3 to 0.4 Equivalents of $Pd(PPh_3)_4$

A solution of polymer 3 (0.06 g) in THF (0.30 mL) was sonicated (VWR Ultrasonics Cleaner (B2500A-MT) (85 W, 42 KHz)) for 5 min. Solid tetrakis(triphenylphosphine)palladium(0) $(Pd(PPh_3)_4)$ (1.4 mg, 1.2 μmol, 0.4 equiv) was added in one portion to the polymer solution at 23° C. The polymer solution was agitated gently with wrist-action swirling for 1 min. After standing for an additional 4 min, an aliquot of the solution (0.2 mL) was withdrawn and was diluted with THF (1.5 mL); this sample was used directly for GPC analysis. Additional aliquots were removed at various time points to follow the conversion of polymer 3 to phthaldialdehyde over time. The extent of depolymerization was measured by integrating the area of the phthaldialdehyde monomer peak relative to that of the peak for polymer 3. A similar procedure was used to monitor the behavior of polymer 4 in response to $Pd(PPh_3)_4$, and to evaluate the effect of quantity of $Pd(PPh_3)_4$.

c. Evaluating the Response of Polymer 6 to UV Light

A quartz flask containing a solution of polymer 6 (0.02 g) in THF (15 mL) was cooled to 0° C. in an ice bath. Dry ice was placed on the lowest level inside the Uvitron International INTELLI-RAY 600 UV light box to cool the surrounding air and minimize the accumulation of heat within the box during irradiation. The 0° C. reaction solution was irradiated with UV light (intensity set at 100%), and the 0° C. ice bath was changed every 500 s. An aliquot of the reaction solution (1 mL) was collected and warmed to 23° C. After 30 min at 23° C., the sample was injected into the GPC.

d. Evaluating the Response of Polymer 7 to UV Light

Polymer 7 was tested using the same procedure described for polymer 6.

e. Evaluating the Response of Polymer 5 to Fluoride

Preparation of TBAF solution in THF-phosphate buffer: A solution (1 mL) of tetrabutylammonium fluoride in THF (1.0 M) was diluted with an aqueous solution of phosphate buffer (0.1 M, 2 mL). This aqueous solution was prepared by dissolving dibasic potassium phosphate (0.72 g, 4.1 mmol) in 40 mL of deionized water; the pH was adjusted to 7.1 with aqueous HCl (1.0 N).

A solution of polymer 5 (0.04 g) in THF (0.26 mL) was sonicated for 5 min. A solution of TBAF in THF-phosphate buffer (4.0 μL, 1.3 μmol, 0.5 equiv) was added to the polymer solution at 23° C. The reaction mixture was agitated gently with wrist-action swirling for 1 min. An aliquot (0.2 mL) of this reaction mixture was diluted with THF (1.5 mL) and then was injected into the GPC.

4. Fabrication and Testing of Mixed Poly(Phthalaldehyde) Films a. Fabrication

Silicon molds were prepared on microscope glass slides. A solution of polymer 4 (0.45 g, Mn: 30.3 KDa) in 1,4-dioxane (1.5 mL) was sonicated VWR Ultrasonics Cleaner (B2500A-MT) (85 W, 42 KHz) until the polymer solution became homogenous (approximately 30 min). The polymer solution (0.7 mL) was deposited onto the glass slide using a syringe. After drying for 24 h at 23° C. under an atmosphere of air, a 6 mm-diameter circle was cut out of the film using a $CO_2$ laser cutter (laser frequency: 230 Hz). A solution of polymer 5 (0.2 g, Mn: 27.9 KDa) in 1,4-dioxane (0.6 mL) was sonicated for 15 min using the same sonicator and settings as described previously. The solution of polymer 5 (40 μl.) was deposited inside the circle with a syringe. The film spread evenly and was dried for 24 h at 23° C. under an atmosphere of air.

b. Testing

The dried film was cut from the mold using a razor blade. The film was peeled off of the glass slide and placed on a new glass slide. The film had the following dimensions: 14.6 mm (h)×13.4 mm (w)×490 μm (thickness). Film weight: 0.065 g.

The film was placed in a beaker that contained ethyl acetate (4.0 mL) at 23° C. After 10 minutes, a solution of TBAF (0.3 M, 1.8 mL, 0.6 mmol, approximately $1.3 \times 10^3$ equiv; see preparation above) in THF-PBS buffer was added to the ethyl acetate. The beaker was agitated gently with wrist-action swirling for 5 min, and then again for 1 min at 5 min intervals until the depolymerization of polymer 5 was complete (this depolymerization process required approximately 15 min). A white circle developed in the area of the film where polymer 5 was depolymerizing; the surrounding polymer 4 remained colorless and intact. As the depolymerization of polymer 5 continued, a hole developed in the center of the film. After 15 min of total reaction time, the film was removed from the ethyl acetate, rinsed with diethyl ether (4×5 mL) and dried at 23° C. under an atmosphere of air.

The results of this test are depicted in FIG. 4. For example, the film in FIG. 4B contains polymer 5 patterned as a circle within a film of polymer 4 (the overall dimensions of the sheet are 14.6 mm×13.4 mm×490 μm). Since polymers 4 and 5 are 95% identical in chemical composition, they do not phase segregate, and the sheet appears to be homogenous upon visual inspection. When the film is immersed in ethyl acetate (4 mL) and exposed to a solution of tetrabutylammonium fluoride (0.3 M, 0.6 mL in 1:2 THF-phosphate buffer, 0.1 M, pH 7.1), polymer 5 depolymerizes completely within 15 min. Partial depolymerization is visible in FIG. 4C. After complete depolymerization (15 min), the film was rinsed with diethyl ether (FIG. 4D).

5. Production of Colorimetric or Fluorescent Readouts Upon Depolymerization

Poly(phthalaldehyde) and its derivatives may yield unpolymerized monomer derivatives that are colored and/or fluorescent, but that when they were polymers were non-colored/non-fluorescent. This allows detection of depolymerization (and therefore of the presence of the triggering substance) by straightforward detection of a production of color or fluorescence. This allows embodiments of the invention to be used as analyte detection and signal amplification reagents.

Figure 7:
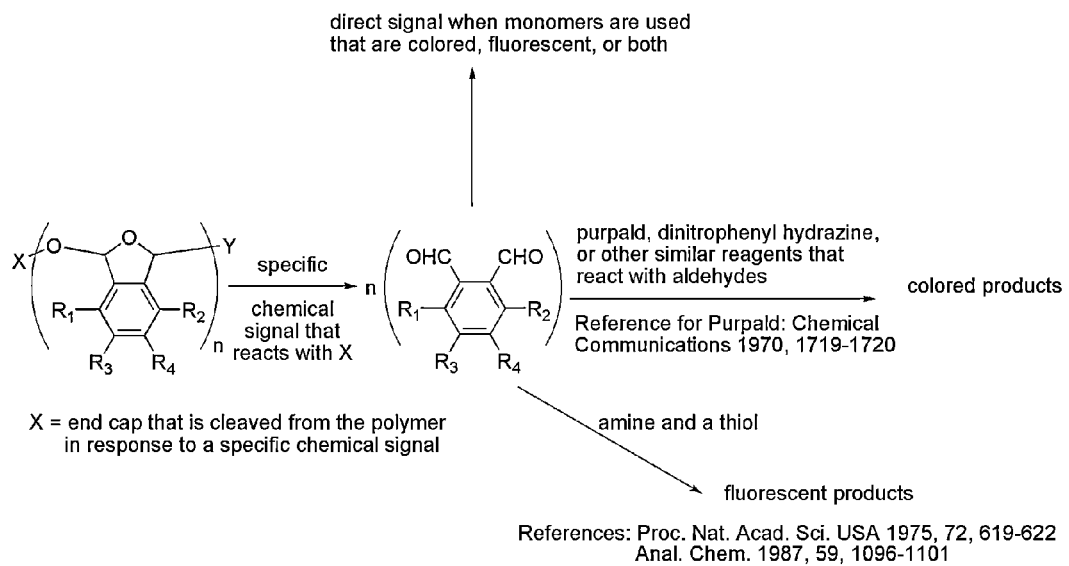
FIG. 7 shows a method for producing a colorimetric or fluorescent readout upon depolymerization.

Three methods of this type are illustrated in FIG. 7. In that figure, R1, R2, R3, and R4 are independently selected and may be, for example, hydrogen, OMe, O-alkyl, or O-aryl. A direct readout of depolymerization is obtained with poly(phthalaldehyde) since the polymer is colorless, but the monomer (1,2-benzene dicarboxyaldehyde) is yellow. Similarly, if 1,2-napthalene dialdehydes are used, the monomers are fluorescent and colored. As illustrated below, the polymers (and the monomers that are used to make them) can vary substantially in structure, which gives rise to monomers upon depolymerization that vary in color, intensity of color, and fluorescence.

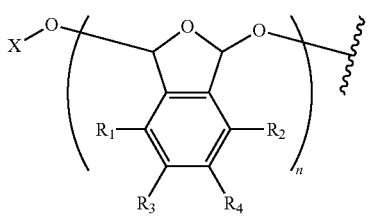

$R_1$, $R_2$, $R_3$, and $R_4$ are independently selected and may be H, or OMe, or O-Alkyl, or O-Aryl

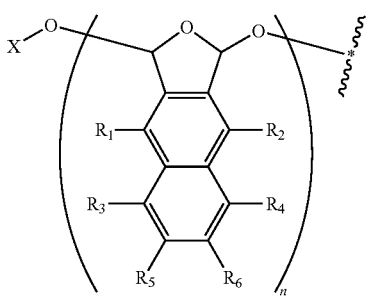

$R_1$-$R_6$ are independently selected and may be H, or OMe, or O-Alkyl, or O-Aryl.

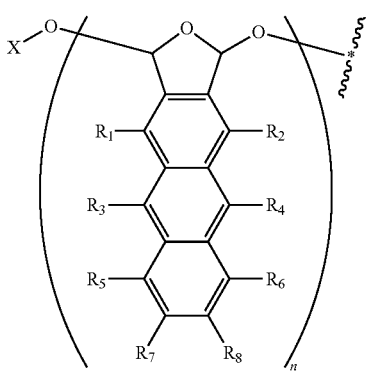

$R_1$-$R_8$ are independently selected and may be H, or OMe, or O-Alkyl, or O-Aryl.

The second method of providing a readout that is illustrated in FIG. 7 involves addition of a reagent after depolymerization. This reagent can be Purpald, dinitrophenyl hydrazine, or any other reagent that reacts with an aldehyde to produce a colorimetric or fluorescent product. Similarly, the third method involves adding a thiol (e.g., 2-mercaptoethanol, although other thiols will work as well) and an amine (e.g., aniline, although any primary or secondary amine, or aniline will work) that together convert 1,2-dialdehydes into fluorescent products. The amine and the thiol are added after the signal causes depolymerization of the polymer.

B. Poly(Aldehydes)

Poly(aldehydes) with capping and triggering groups according to embodiments of the invention may be prepared. These compounds may have many useful properties. For example, poly(aldehydes), like poly(phthalaldehyde) and its other derivatives, may provide monomer derivatives that are colored and/or fluorescent, but polymers that are non-colored/non-fluorescent. This allows detection of depolymerization (and therefore of the presence of the triggering substance) by straightforward detection of a disappearance of color or fluorescence.

Additional poly(aldehydes) may have the following formula:

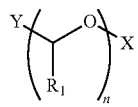

where X may be, for example, $R_3SiO$—, $(RO)_2B$—, $CH_2CHCH_2OCO_2$—, monosaccharide-O— (i.e., a single sugar unit, including both natural and unnatural sugars; an example is a beta-D-glucuronic acid unit, which is cleaved at the anomeric position by the enzyme beta-D-glucuronidase), polysaccharide-O— (i.e., multiple sugar units linked together, both as linear and branched polysaccharides, including, but limited to glycosaminoglycans; an example is starch, which is cleaved at the anomeric position by amylase), or peptide-NH— (i.e., a specific peptide sequence comprised of natural amino acids, unnatural amino acids, or both, and including peptidomimetics that are recognized as substrates by specific proteases; an example peptide is alanine-phenylalanine, which is cleaved by chymotrypsin at the carboxy terminus of the peptide). Y is a functionality arising from addition of an anhydride (e.g., $Ac_2O$), isocyanate (e.g., PhNCO), alkylating reagent (e.g., methyl iodide), acid chloride (e.g., AcCl), chloroformate (e.g., $ClCO_2Ph$), or acid fluoride (e.g., AcF) to the end of the polymer. Z, therefore, would be an ether (e.g., polymer-OMe), an ester (e.g., polymer-$OCOCH_3$), a carbamate (e.g., polymer-OCONHPh), or a carbonate (e.g., polymer-$OCO_2Ph$). $R_1$ is selected from the group consisting of branched or linear C1-C15 alkyl and heteroatom-functionalized alkyl chains, and branched or linear C1-C15 pyridines.

The following are examples of poly(aldehydes) that may be made according to embodiments of the invention. In each case X may be, for example, $R_3SiO$—, $(RO)_2B$—, $CH_2CHCH_2OCO_2$—, monosaccharide-O— (i.e., a single sugar unit, including both natural and unnatural sugars; an example is a beta-D-glucuronic acid unit, which is cleaved at the anomeric position by the enzyme beta-D-glucuronidase), polysaccharide-O— (i.e., multiple sugar units linked together, both as linear and branched polysaccharides, including, but limited to glycosaminoglycans; an example is starch, which is cleaved at the anomeric position by amylase), or peptide-NH— (i.e., a specific peptide sequence comprised of natural amino acids, unnatural amino acids, or both, and including peptidomimetics that are recognized as substrates by specific proteases; an example peptide is alanine-phenylalanine, which is cleaved by chymotrypsin at the carboxy terminus of the peptide). Y is a functionality arising from addition of an anhydride (e.g., $Ac_2O$), isocyanate (e.g., PhNCO), alkylating reagent (e.g., methyl iodide), acid chloride (e.g., AcCl), chloroformate (e.g., $ClCO_2Ph$), or acid fluoride (e.g., AcF) to the end of the polymer. Z, therefore, would be an ether (e.g., polymer-OMe), an ester (e.g., polymer-$OCOCH_3$), a carbamate (e.g., polymer-OCONHPh), or a carbonate (e.g., polymer-$OCO_2Ph$). $R_1$ is selected from the group consisting of branched or linear C1-C15 alkyl and heteroatom-functionalized alkyl chains, and branched or linear C1-C15 pyridines.

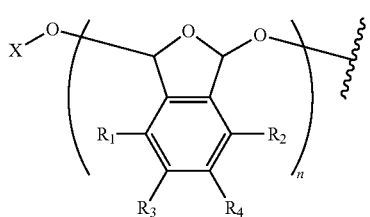

$R_1$, $R_2$, $R_3$, and $R_4$ are independently selected and may be H, or OMe, or O-Alkyl, or O-Aryl

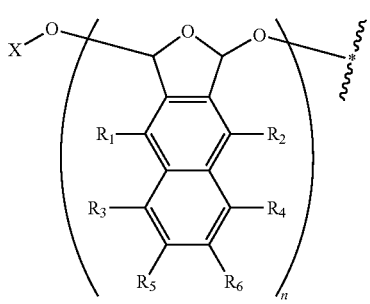

$R_1$-$R_6$ are independently selected and may be H, or OMe, or O-Alkyl, or O-Aryl.

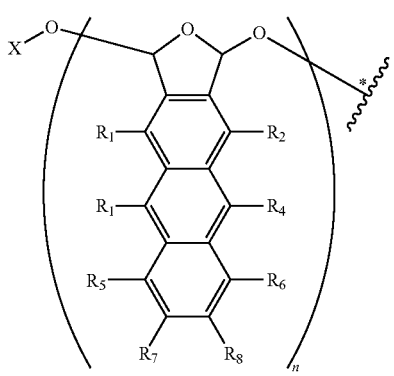

$R_1$-$R_8$ are independently selected and may be H, or OMe, or O-Alkyl, or O-Aryl.

C. Poly(Ethers)

Figure 8:
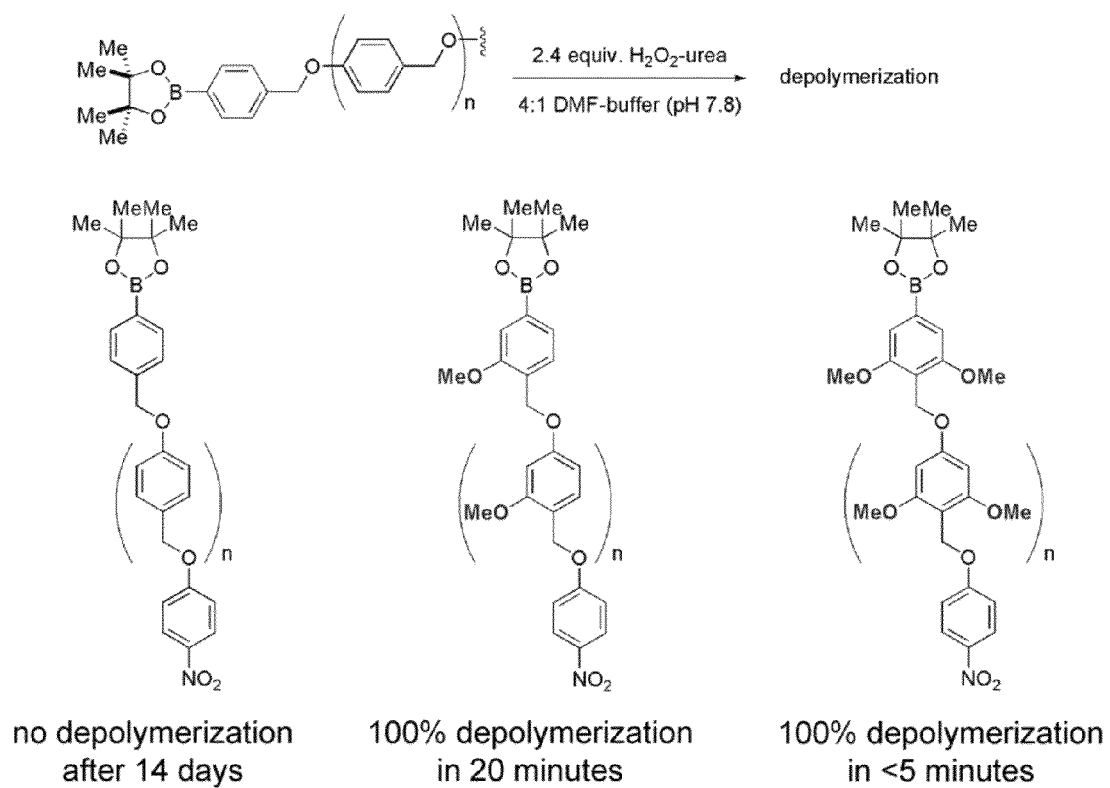
FIG. 8 shows the effect of inclusion of methyl ethers on the aromatic ring of the repeating unit in a poly(ether).
Figure 9:
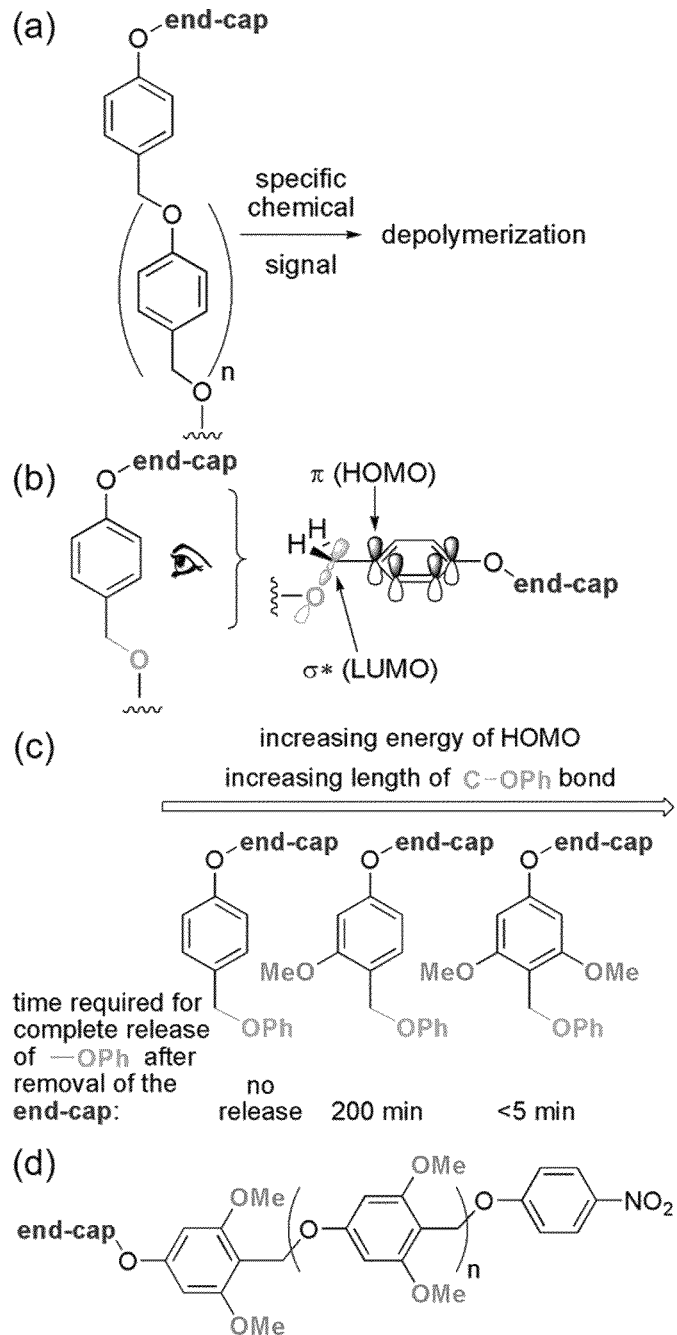
FIG. 9 shows one possible theoretical underpinning for the effect shown in FIG. 8.

Poly(ethers) including triggers that enable depolymerization in the presence of a signal are also included herein. Short oligomers and dendrimers of poly(ethers) are known to degrade under basic conditions in response to applied chemical signals, but because these short oligomers and dendrimers degrade under basic conditions, they do not teach how to prepare polymers that depolymerize to applied signals under neutral conditions. As shown in FIGS. 8 and 9, we have discovered that electron donating groups in each repeating unit of a poly(ether) allow rapid release of each monomer unit under neutral (pH 7) conditions (as well as basic and acidic conditions) as the polymer depolymerizes in a step-wise fashion. We believe that this discovery is a new invention that enables the conception and preparation of poly(ethers) that are capable of depolymerizing to all varieties of specific applied signals in a broad range of solvents and under a broad range of conditions, including acidic, basic, and neutral pH values.

1. Compounds

Poly(ethers) of the invention include those having one of the following formulas:

W and Z represent atoms in an aromatic ring:

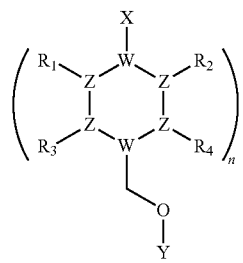

W=carbon
Z=is independently selected and may be carbon, nitrogen, oxygen, or sulfur $R_1$, $R_2$, $R_3$, and $R_4$ are independently selected and may be H, or OMe, or O-Alkyl (C1-C30, linear or branched), O-polyethylene glycol (1-30 repeating units), or O-Aryl X=functionality that cleaves in the presence of a specific chemical signal. Examples include $R_3SiO$— (R may be C1-C30 linear and branched alkyl groups, aryl groups), $(RO)_2B$—, $CH_2CHCH_2OCO_2$—, monosaccharide-O—, polysaccharide-O—, or peptide-NH—.

Y=esters (e.g. $CH_3CO$—), carbonates (e.g., $CH_3OCO$—), carbamates (e.g., $CH_3NHCO$—), ethers (e.g., $CH_3$—), H, or functionality that releases more of the chemical signal that reacts with X, e.g.:

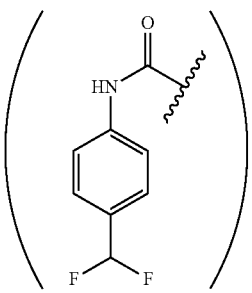

W and Z represent atoms in an aromatic ring:

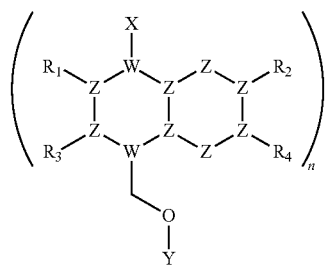

W=carbon
Z=is independently selected and may be carbon, nitrogen, oxygen, or sulfur $R_1$, $R_2$, $R_3$, and $R_4$ are independently selected and may be H, or OMe, or O-Alkyl (C1-C30, linear or branched), O-polyethylene glycol (1-30 repeating units), or O-Aryl X=functionality that cleaves in the presence of a specific chemical signal. Examples include $R_3SiO-$ (R may be C1-C30 linear and branched alkyl groups, aryl groups), $(RO)_2B-$, $CH_2CHCH_2OCO_2-$, monosaccharide-O—, polysaccharide-O—, or peptide-NH—.

Y=esters (e.g. $CH_3CO-$), carbonates (e.g., $CH_3OCO-$), carbamates (e.g., $CH_3NHCO-$), ethers (e.g., $CH_3-$), H, or functionality that releases more of the chemical signal that reacts with X, e.g.:

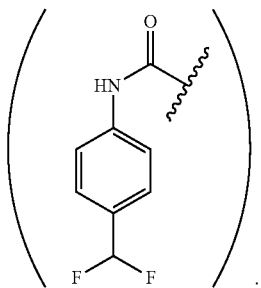

W and Z represent atoms in an aromatic ring:

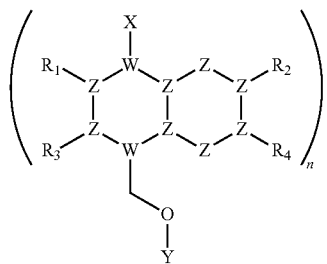

W=carbon

Z=is independently selected and may be carbon, nitrogen, oxygen, or sulfur $R_1$, $R_2$, $R_3$, and $R_4$ are independently selected and may be H, or OMe, or O-Alkyl (C1-C30, linear or branched), O-polyethylene glycol (1-30 repeating units), or O-Aryl X=functionality that cleaves in the presence of a specific chemical signal. Examples include $R_3SiO-$ (R may be C1-C30 linear and branched alkyl groups, aryl groups), $(RO)_2B-$, $CH_2CHCH_2OCO_2-$, monosaccharide-O—, polysaccharide-O—, or peptide-NH—.

Y=esters (e.g. $CH_3CO-$), carbonates (e.g., $CH_3OCO-$), carbamates (e.g., $CH_3NHCO-$), ethers (e.g., $CH_3-$), H, or functionality that releases more of the chemical signal that reacts with X, e.g.:

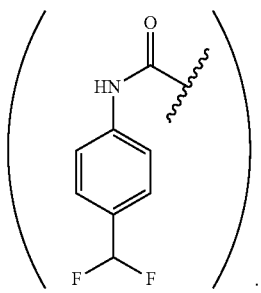

In each case X may be, for example, $R_3SiO-$, $(RO)_2B-$, $CH_2CHCH_2OCO_2-$, monosaccharide-O— (i.e., a single sugar unit, including both natural and unnatural sugars; an example is a beta-D-glucuronic acid unit, which is cleaved at the anomeric position by the enzyme beta-D-glucuronidase), polysaccharide-O— (i.e., multiple sugar units linked together, both as linear and branched polysaccharides, including, but limited to glycosaminoglycans; an example is starch, which is cleaved at the anomeric position by amylase), or peptide-NH— (i.e., a specific peptide sequence comprised of natural amino acids, unnatural amino acids, or both, and including peptidomimetics that are recognized as substrates by specific proteases; an example peptide is alanine-phenylalanine, which is cleaved by chymotrypsin at the carboxy terminus of the peptide). Y is a functionality arising from addition of an anhydride (e.g., $Ac_2O$), isocyanate (e.g., PhNCO), alkylating reagent (e.g., methyl iodide), acid chloride (e.g., AcCl), chloroformate (e.g., $ClCO_2Ph$), or acid fluoride (e.g., AcF) to the end of the polymer. Z, therefore, would be an ether (e.g., polymer-OMe), an ester (e.g., polymer-$OCOCH_3$), a carbamate (e.g., polymer-OCONHPh), or a carbonate (e.g., polymer-$OCO_2Ph$). $R_1$ is selected from the group consisting of branched or linear C1-C15 alkyl and heteroatom-functionalized alkyl chains, and branched or linear C1-C15 pyridines.

2. Synthesis

Typically, poly(ethers) of the invention may be synthesized by three general methods. Method 1 is a step-wise synthesis in which monomer units are appended sequentially to the growing end of the polymer chain. Method 2 is a metal-catalyzed polymerization reaction in which monomers contain both a benzylic alcohol and aryl halide functionality. Method 3 is a similar metal-catalyzed polymerization in which two monomers are used simultaneously: one monomer contains a trigger and a benzyl alcohol and serves as the terminus of a polymer chain, and the other monomer contains both a benzylic alcohol and aryl halide functionality to enable the polymerization reaction.

Figure 10:
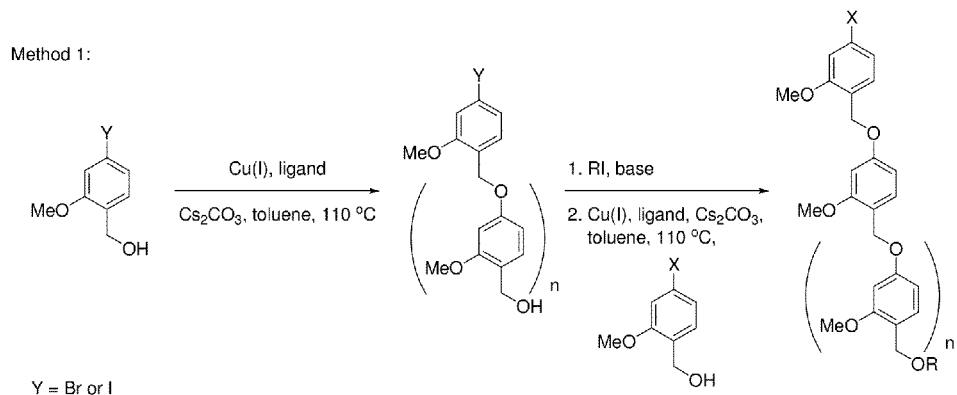
FIGS. 10, 11, and 12 show synthesis routes for a one-methoxy poly(ether).
Figure 11:
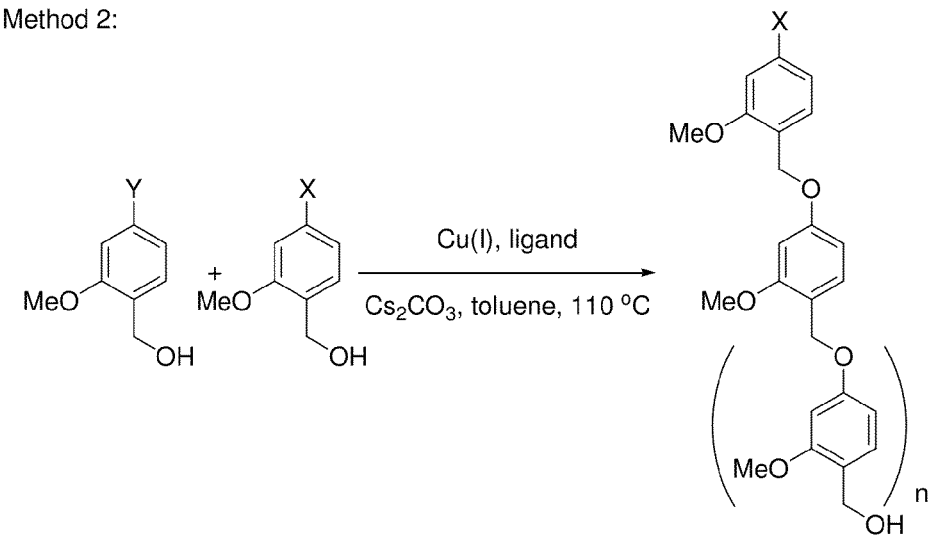
Figure 12:
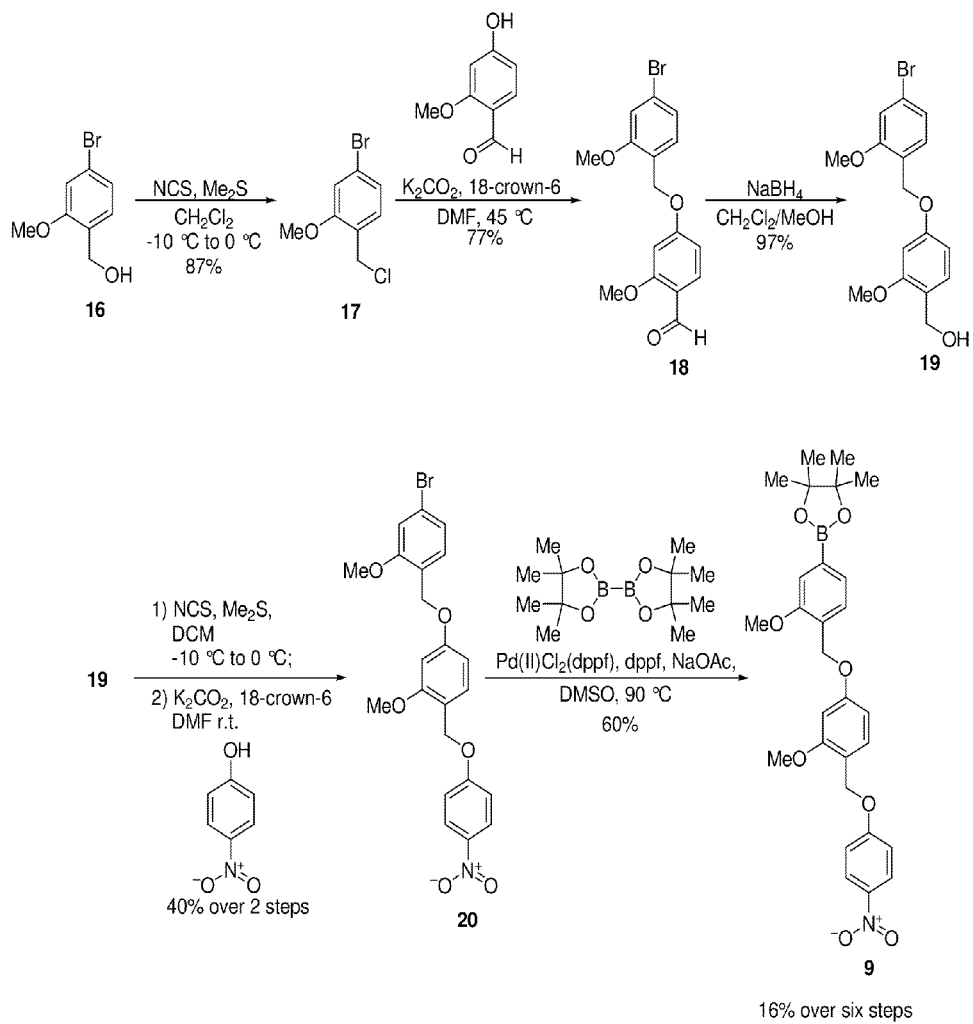
Figure 13:
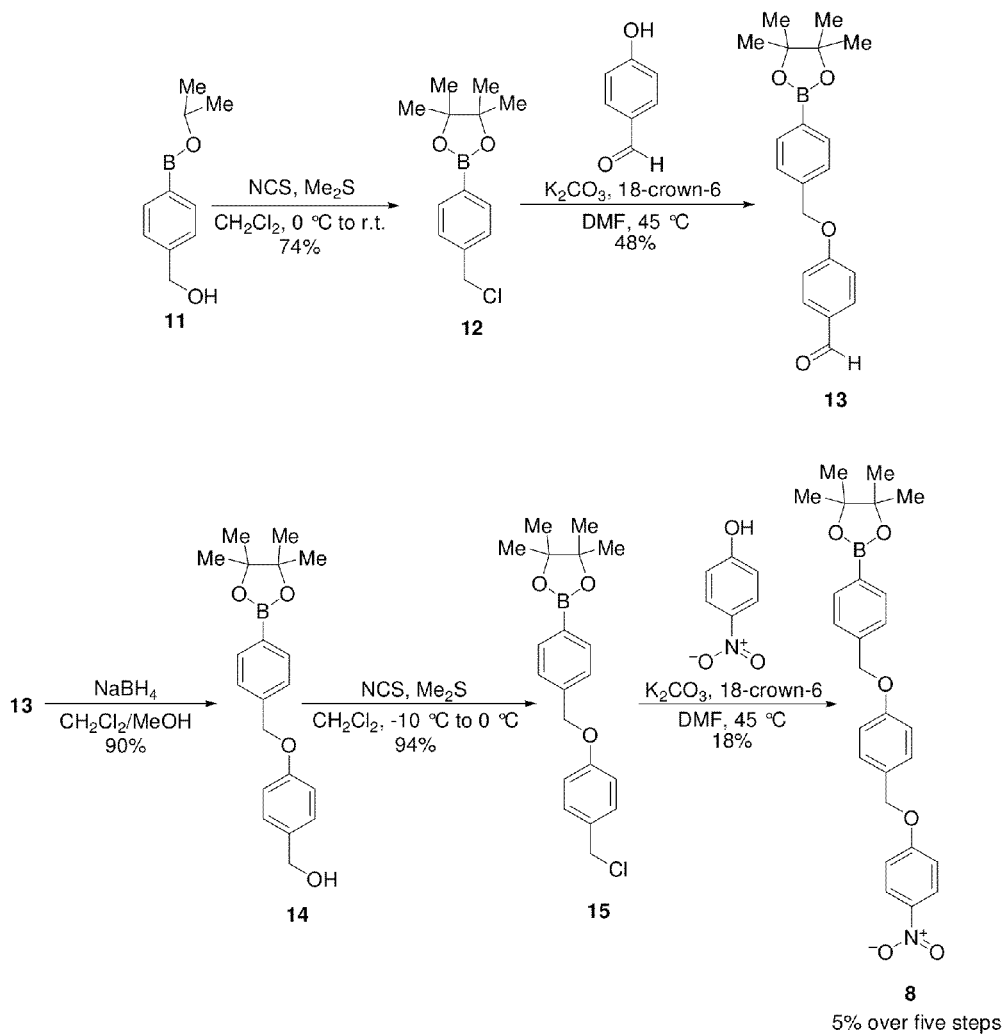
FIG. 13 shows a synthesis route for a non-substituted poly(ether).

Example inventive synthesis schemes for poly(ethers) according to embodiments of the invention are given in FIGS. 10, 11, and 12 (for a one-methoxy oligomer) and FIG. 13 (for a no-methoxy oligomer), and FIG. 14 (for a two-methoxy oligomer).

Another example inventive procedure for synthesis of a depolymerizable poly(ether) is set forth below.

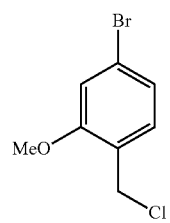

1

N-chlorosuccinimide (0.734 g, 5.50 mmol, 1.1 equiv.) was dissolved in dichloromethane (10 mL) at 0° C., and dimethyl sulfide (0.441 mL, 6.00 mmol, 1.2 equiv.) was added in one portion forming a precipitate. The solution was then chilled to −20° C. and stirred for 10 minutes. A solution of 4-bormo-2-methoxybenzyl alcohol (1.09 g, 5.00 mmol, 1 equiv.) in dichloromethane (15 mL) was added dropwise. The reaction mixture was stirred for 3 h until the precipitate disappeared. The solution was washed with cold brine and the layers separated. The aqueous layer was extracted with ethyl acetate, and the combined organic layers were dried with sodium sulfate. The solution was concentrated under reduced pressure and purified via column chromatography on SiO$_2$ (elution with 10% ethyl acetate/hexanes) to afford compound 1 as a white solid (0.976 g, 4.50 mmol, 90%). $^1$H NMR (CDCl$_3$): δ 7.211 (d, 1H, J=8 Hz), 7.085 (dd, 1H, J=8, 2 Hz), 7.024 (d, 1H, J=2 Hz), 4.583 (s, 2H), 3.869 (s, 3H); $^{13}$C NMR (CDCl$_3$): δ 158.0, 131.7, 125.1, 123.9, 123.5, 114.6, 56.0, 41.0.

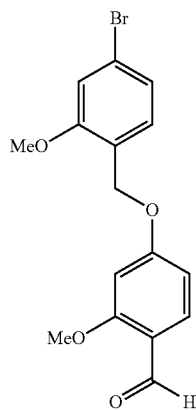

2

1 (0.868 g, 4.00 mmol, 1 equiv.), 4-hydroxy-2-methoxybenzaldehyde (0.730 g, 4.80 mmol, 1.2 equiv.), 18-crown-6 (0.106 g, 0.400 mmol, 0.1 equiv.), potassium carbonate (1.10 g, 8.00 mmol, 2 equiv.) were dissovled in dimethylformamide (20 mL). The reaction mixture was heated to 40° C. and stirred for 24 h. The solvent was removed under reduced pressure, and the resulting residue was re-dissolved in ethyl acetate (40 mL). The solution was washed with water (30 mL) followed by a saturated sodium chloride solution (30 mL). The organic layer was dried over sodium sulfate, concentrated under reduced pressure, and purified by via column chromatography on SiO$_2$ (gradient elution with 10% ethyl acetate/hexanes to 20% ethyl acetate/hexanes) to afford compound 2 as a white solid (1.08 g, 3.08 mmol, 77%). IR (cm$^{-1}$): 2925, 2866, 1664, 1595, 1262 1241, 1028, 853; $^1$H NMR (CDCl$_3$): δ 7.802 (d, 1H, J=9), 7.289 (d, 1H, J=8 Hz), 7.127 (dd, 1H, J=8, 2 Hz), 7.059 (d, 1H, J=2), 6.612 (dd, 1H, J=9, 2 Hz), 6.534 (d, 1H, J=2 Hz), 5.102 (s, 2H), 3.892 (s, 3H), 3.870 (s, 3H); $^{13}$C NMR (CDCl$_3$): δ 188.7, 165.7, 164.0, 157.8, 131.1, 130.3, 124.2, 123.9, 123.2, 119.6, 114.5, 106.9, 99.2, 65.2, 56.2, 56.0.

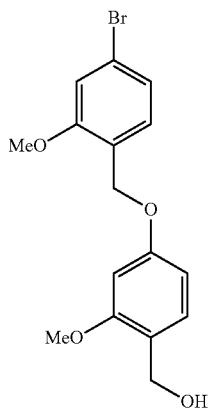

3

2 (1.05 g, 2.99 mmol, 1 equiv.) was dissolved in dichloromethane (25 mL) and methanol (15 mL). To the solution was added sodium borohydride (0.227 g, 6.00 mmol, 2 equiv.) in two batches over 1 h at 20° C. After stirring for 2 h, the reaction was quenched with water (10 mL) and stirred for 10 minutes. The mixture was diluted with ethyl acetate (75 mL) and washed with a saturated solution of sodium chloride (30 mL). The aqueous layer was extracted with ethyl acetate (2×75 mL). The combined organic layers were dried with sodium sulfate, concentrated under reduced pressure to afford 3 as a white solid (0.995 g, 2.76 mmol, 92%) as a white solid. IR (cm$^{-1}$): 3316, 2930, 2830, 1589, 1490, 1241, 1201, 1027, 1000, 822; $^1$H NMR (CDCl$_3$): δ 7.300 (d, 1H, J=8 Hz), 7.139 (d, 1H, J=8 Hz), 7.098 (dd, 1H, J=8, 2 Hz), 7.024 (d, 1H, J=2 Hz), 6.539 (d, 1H, J=2 Hz), 6.493 (dd, 1H, J=8, 2 Hz), 5.018 (s, 2H), 4.594 (s, 2H), 3.820 (s, 3H), 3.772 (s, 3H).

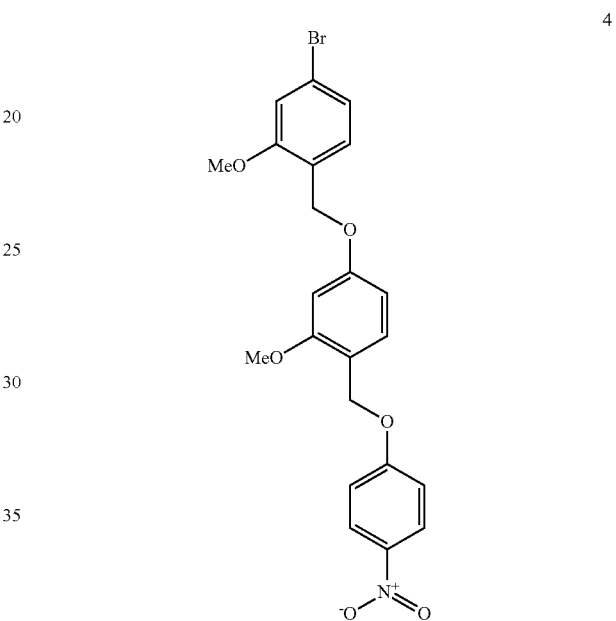

4

N-chlorosuccinimide (0.235 g, 1.76 mmol, 1.1 equiv.) was dissolved in dichloromethane (5 mL) at 0° C., and dimethyl sulfide (0.846 mL, 1.92 mmol, 1.2 equiv.) was added in one portion forming a precipitate. The solution was then chilled to −20° C. and stirred for 10 minutes. A solution of 3 (0.565 g, 1.60 mmol, 1 equiv.) in dichloromethane (5 mL) was added dropwise. The reaction mixture was stirred for 1.5 h until the precipitate disappeared. The solution was washed with cold sodium chloride solution (10 mL) and the aqueous layer was extracted with dichloromethane (2×20 mL). The combined organic layers were dried with sodium sulfate and the solution was concentrated under reduced pressure. The residue was re-dissolved in dimethylformamide (7 mL). 4-Nitrophenol (0.290 g, 2.09 mmol, 1.3 equiv.), 18-crown-6 (0.037 g, 0.14 mmol, 0.09 equiv.), and potassium carbonate (0.384 g, 2.78 mmol, 1.7 equiv.) were added in one batch. The reaction mixture was heated to 30° C. and stirred for 24 h. The solvent was removed under reduced pressure, and the resulting residue re-dissolved in ethyl acetate (30 mL) and washed with a sodium chloride solution (5×15 mL). The organic layer was dried with sodium sulfate, concentrated under reduced pressure, and purified via column chromatography on SiO$_2$ (eluting with 10% ethyl acetate/hexanes) to afford compound 4 as a white solid (0.220 g, 0.464 mmol, 33%). $^1$H NMR (CDCl$_3$): δ 8.167 (d, 2H, J=9 Hz), 7.316-7.2534 (m, 2H), 7.099 (d, 1H, J=8 Hz), 7.085-6.994 (m, 3H), 6.576-6.542 (m, 2H), 5.096 (s, 2H), 5.031 (s, 2H), 3.842 (s, 3H), 3.825 (s, 3H).

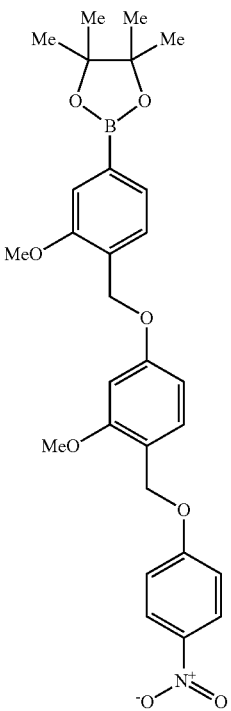

4 (0.363 g, 0.766 mmol, 1 equiv.), 1,1'-Bis(diphenylphosphino)ferrocene-palladium(II)dichloride 1:1 dichloromethane adduct (0.0313 g, 0.0383 mmol, 0.05 equiv.), 1'-Bis(diphenylphosphino)ferrocene (0.0212 g, 0.0383 mmol, 0.05 equiv.), sodium acetate (0.376 g, 3.83 mmol, 5 equiv.), bis(pinacol) diboron (0.233 g, 0.919 mmol, 1.2 equiv.) were dried under reduced pressure for 24 h before being dissovled in dimethyl sulfoxide (3 mL). The reaction mixture was heated to 90° C. and stirred for 20 h. The reaction mixture was diluted with ethyl acetate (50 mL) and filtered through a plug of $SiO_2$ and Celite® 454. The solution was washed with a sodium chloride solution (6×25 mL). The organic layer was dried with sodium sulfate, concentrated under reduced pressure, and purified via column chromatography on $SiO_2$ (gradient elution with hexanes to 10% ethyl acetate/hexanes) to afford compound 5 as a white solid (0.239 g, 0.458 mmol, 60%). $^1$H NMR ($CDCl_3$): δ 8,175 (m, 2H), 7.449 (dd, 2H, J=19, 7 Hz), 7.318 (s, 1H), 7.247 (m, 1H), 7.012 (m, 2H), 6.602 (d, 1H, J=2), 6.564 (dd, 1H, J=8, 2 Hz); $^{13}$C NMR ($CDCl_3$): δ 164.3, 160.7, 158.5, 156.2, 141.5, 130.5, 128.5, 127.8, 127.5, 126.0, 116.2, 115.8, 114.9, 105.7, 99.5, 84.0, 65.9, 65.2, 55.6, 25.0.

3. Results

We found that the speed at which a poly(ether) depolymerized at neutral conditions (i.e., at pH of about 7, in water) when subjected to its relevant signal depended significantly on the presence and location of electron donating groups (e.g., methyl ethers (—OMe)) on the aromatic ring of the repeating unit. This is illustrated in FIGS. 8 and 9. In those figures an exemplary chemical signal (hydrogen peroxide) cleaves an exemplary end-cap (aryl boronate). Although applicant does not wish to be bound by theory, the forces that are believed to result in this effect are illustrated in FIG. 9.

D. Depolymerizable Poly(Ether) Cross-Linkers

Although useful as depolymerizable polymers in their own right, depolymerizable poly(ethers) may also serve as cross-linkers for other polymers. Upon exposure to the appropriate depolymerization signal, the poly(ethers) depolymerize, allowing the previously cross-linked polymers to revert to the status of single-polymer chains. This cross-linked polymer would have many uses, including in low-energy plastic recycling.

In exemplary embodiments the cross-linked polymer is a poly(methylmethacrylate), poly(styrene), poly(methacrylate), poly(urethane), poly(ester), or polymers derived from acrylic acid, 4-vinyl pyridine, 2-vinyl pyridine, acrylonitrile, acrylamide, 2-acrylamido-2-methylpropane sulfonic acid, urocanic ethyl ester, (hydroxyethyl)methacrylate, 2-(diethylamino)ethylmethacrylate. The depolymerizable poly(ether) can be attached as a cross-linker to other polymers as an amide, ester, imide, carbon-carbon bond, ether, or through a Huisgen cyclization.

In additional embodiments, the poly(ether) cross-linker may be used to cross-link one or more depolymerizable polymers. The cross-linker and the polymer(s) could depolymerize in response to the same chemical signal, or different chemical signals. In one example, the cross-linker would respond to a specific signal to release the cross-linked polymers, and then the cross-linked polymers would respond to a different signal to depolymerize to monomers.

There are many possible uses of these depolymerizable cross-linkers, but the primary function would be to switch a rigid material into a more flexible material. Other applications include low-energy recycling processes, even for highly cross-linked polymers. Selected embodiments of polymers cross-linked by depolymerizable poly(ethers) are shown in FIG. 15.

E. Depolymerizable Copolymers

Although embodiments of the invention have so far been discussed in the context of depolymerizable polymers, depolymerizable copolymers are also contemplated. These copolymers enable an artisan to tune various properties of the resulting substance, including hydrophobicity, hydrophilicity, wetting, and rheology.

One signal-responsive copolymer is shown in the formula

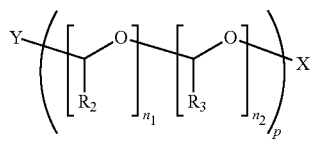

$R_2$ and $R_3$ are different and may be branched or linear $C_1$-$C_{15}$ alkyl and heteroatom-functionalized alkyl chains, and branched or linear C1-C15 pyridines; X may be, for example, $R_3SiO$—, $(RO)_2B$—, $CH_2CHCH_2OCO_2$—, monosaccharide-O— (i.e., a single sugar unit, including both natural and unnatural sugars; an example is a beta-D-glucuronic acid unit, which is cleaved at the anomeric position by the enzyme beta-D-glucuronidase), polysaccharide-O— (i.e., multiple sugar units linked together, both as linear and branched polysaccharides, including, but limited to glycosaminoglycans; an example is starch, which is cleaved at the anomeric position by amylase), or peptide-NH— (i.e., a specific peptide sequence comprised of natural amino acids, unnatural amino acids, or both, and including peptidomimetics that are recognized as substrates by specific proteases; an example peptide is alanine-phenylalanine, which is cleaved by chymotrypsin at the carboxy terminus of the peptide). Y is a functionality arising from addition of an anhydride (e.g., $Ac_2O$), isocyanate (e.g., PhNCO), alkylating reagent (e.g., methyl iodide), acid chloride (e.g., AcCl), chloroformate (e.g., ClCO$_2$Ph), or acid fluoride (e.g., AcF) to the end of the polymer. Z, therefore, would be an ether (e.g., polymer-OMe), an ester (e.g., polymer-OCOCH$_3$), a carbamate (e.g., polymer-OCONHPh), or a carbonate (e.g., polymer-OCO$_2$Ph). $R_1$ is selected from the group consisting of branched or linear C1-C15 alkyl and heteroatom-functionalized alkyl chains, and branched or linear C1-C15 pyridines. Both n1 and n2 are independently selected and are between 1 and 500 and p is between 20 and 1000.

Another embodiment is shown below:

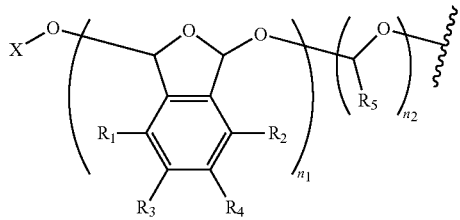

$R_1$, $R_2$, $R_3$, and $R_4$ are independently selected and may be H, OMe, O-Alkyl, or O-Aryl.

$R_5$ is aryl or alkyl.

Patents, patent applications, publications, scientific articles, books, web sites, and other documents and materials referenced or mentioned herein are indicative of the levels of skill of those skilled in the art to which the inventions pertain, as of the date each publication was written, and all are incorporated by reference as if fully rewritten herein. Inclusion of a document in this specification is not an admission that the document represents prior invention or is prior art for any purpose.

We claim:

1. A signal-responsive polymer comprising a polymer that has the following structure:

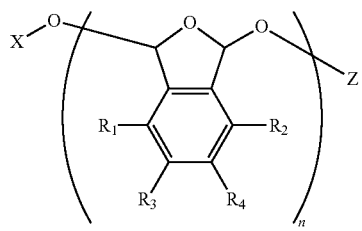

wherein Z is selected from the group consisting of an ether, an ester, a carbamate, and a carbonate;

wherein n is between 5 and 10000;

wherein X is selected from the group consisting of (R)$_3$SiO—, (RO)$_2$B—, wherein R is selected from the group consisting of hydrogen, straight-chain or branched alkyl between 1 and 30 carbon atoms, straight chain or branched aryl between 2 and 30 carbon atoms, an ether, and an ester; CH$_2$CHCH$_2$OCO$_2$—; monosaccharide-O—; polysaccharide-O—; peptide-NH—; ortho-nitrobenzyl; ortho-nitrobenzyl carbamate; and

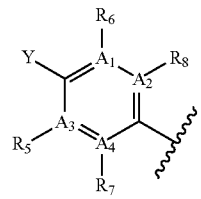

wherein $A_1$, $A_2$, $A_3$, and $A_4$ are independently selected from the group consisting of nitrogen, oxygen, sulfur, and carbon, and wherein when the selection is other than sulfur or carbon the "R" group attached to the selection is not present;

wherein $R_5$, $R_6$, $R_7$, and $R_8$ are selected independently from the group consisting of hydrogen, branched and straight chain alkyl having between one and thirty carbon atoms, and branched and straight chain aryl having between 2 and 30 carbon atoms; and wherein Y is selected from the group consisting of (R)$_3$SiO—, (RO)$_2$B—, CH$_2$CHCH$_2$OCO$_2$—, monosaccharide-O—, polysaccharide-O—, peptide-NH—, ortho-nitrobenzyl, and ortho-nitrobenzyl carbamate, wherein R is selected from the group consisting of hydrogen, straight-chain or branched alkyl between 1 and 30 carbon atoms, straight chain or branched aryl between 2 and 30 carbon atoms, an ether, and an ester; and wherein $R_1$ and $R_2$ are independently selected from the group consisting of hydrogen, branched and straight chain alkyl having between one and thirty carbon atoms, and branched and straight chain aryl having between 2 and 30 carbon atoms; and wherein $R_3$ and $R_4$ are independently selected from the group consisting of hydrogen, branched and straight chain alkyl having between one and thirty carbon atoms, and branched and straight chain aryl having between 2 and 30 carbon atoms; or $R_3$ and $R_4$, together with the carbon atoms to which they are attached, form an optionally substituted aromatic having the formula

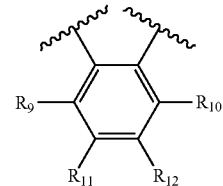

wherein $R_9$ and $R_{10}$ are independently selected from the group consisting of hydrogen, branched and straight chain alkyl having between one and thirty carbon atoms, and branched and straight chain aryl having between 2 and 30 carbon atoms; and wherein $R_{11}$ and $R_{12}$ are independently selected from the group consisting of hydrogen, branched and straight chain alkyl having between 1 and 30 carbon atoms, and branched and straight chain aryl having between 2 and 30 carbon atoms; or $R_{11}$ and $R_{12}$, together with the carbon atoms to which they are attached, form an optionally substituted aromatic having the formula

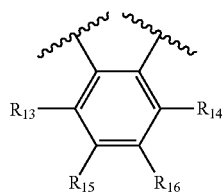

wherein $R_{13}$, $R_{14}$, $R_{15}$, and $R_{16}$ are independently selected from the group consisting of hydrogen, branched and straight chain alkyl having between 1 and 30 carbon atoms, and branched and straight chain aryl having between 2 and 30 carbon atoms;

and an end-cap, wherein cleavage of the end-cap by a specific chemical or physical signal depolymerizes the polymer.

2. A signal-responsive polymer comprising a polymer that has the following structure:

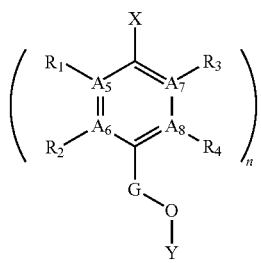

wherein n is between 2 and 1000;

wherein $A_5$, $A_6$, $A_7$, and $A_8$ are independently selected from the group consisting of nitrogen, oxygen, sulfur, and carbon, and wherein when the selection is other than sulfur or carbon the "R" group attached to the selection is not present;

wherein G is selected from the group consisting of a branched and straight chain alkyl group of C1-C30, an ester having the formula CO2R, and an amide having the formula CO2NHR, wherein R is selected from the group consisting of straight-chain or branched alkyl between 1 and 30 carbon atoms and straight chain or branched aryl between 2 and 30 carbon atoms;

wherein Y is selected from the group consisting of an ether, an ester, a carbamate, and a carbonate;

wherein X is selected from the group consisting of $R_3SiO—$, $(RO)_2B—$, $CH_2CHCH_2OCO_2—$, monosaccharide-O—, polysaccharide-O—, peptide-NH—, ortho-nitrobenzyl, ortho-nitrobenzyl carbamate, and

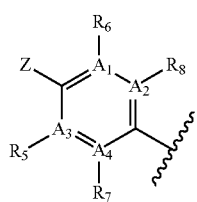

wherein $A_1$, $A_2$, $A_3$, and $A_4$ are independently selected from the group consisting of nitrogen, oxygen, sulfur, and carbon, and wherein when the selection is other than sulfur or carbon the "R" group attached to the selection is not present;

wherein $R_5$, $R_6$, $R_7$, and $R_8$ are selected independently from the group consisting of hydrogen, branched and straight chain alkyl having between one and thirty carbon atoms, and branched and straight chain aryl having between 2 and 30 carbon atoms; and wherein Z is selected from the group consisting of $R_3SiO—$, $(RO)_2B—$, $CH_2CHCH_2OCO_2—$, monosaccharide-O—, polysaccharide-O—, peptide-NH—, ortho-nitrobenzyl, and ortho-nitrobenzyl carbamate; and wherein $R_1$ and $R_2$ are independently selected from the group consisting of hydrogen, branched and straight chain alkyl having between one and thirty carbon atoms, and branched and straight chain aryl having between 2 and 30 carbon atoms; and wherein $R_3$ and $R_4$ are independently selected from the group consisting of hydrogen, branched and straight chain alkyl having between one and thirty carbon atoms, and branched and straight chain aryl having between 2 and 30 carbon atoms; or $R_3$ and $R_4$, together with the carbon atoms to which they are attached, form an optionally substituted aromatic having the formula

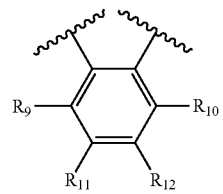

wherein $R_9$ and $R_{10}$ are independently selected from the group consisting of hydrogen, branched and straight chain alkyl having between one and thirty carbon atoms, and branched and straight chain aryl having between 2 and 30 carbon atoms; and wherein $R_{11}$ and $R_{12}$ are independently selected from the group consisting of hydrogen, branched and straight chain alkyl having between 1 and 30 carbon atoms, and branched and straight chain aryl having between 2 and 30 carbon atoms; or $R_{11}$ and $R_{12}$, together with the carbon atoms to which they are attached, form an optionally substituted aromatic having the formula

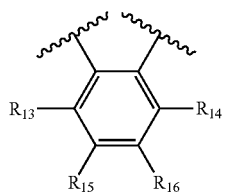

wherein $R_{13}$, $R_{14}$, $R_{15}$, and $R_{16}$ are independently selected from the group consisting of hydrogen, branched and straight chain alkyl having between 1 and 30 carbon atoms, and branched and straight chain aryl having between 2 and 30 carbon atoms;

and an end-cap, wherein cleavage of the end-cap by a specific chemical or physical signal depolymerizes the polymer.

3. A signal-responsive copolymer comprising a copolymer having the following structure:

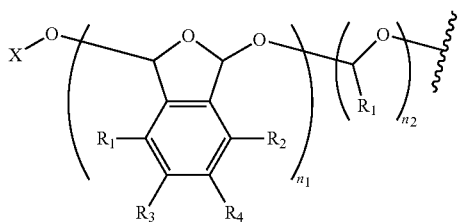

wherein $R_1$, $R_2$, $R_3$, and $R_4$ are independently selected from the group consisting of hydrogen, OMe, O-alkyl, and O-aryl;

$R_5$ is alkyl or aryl; and $n_1$ and $n_2$ are independently selected and between 10 and 10000;

and an end-cap, wherein cleavage of the end-cap by a specific chemical or physical signal depolymerizes the polymer.

4. A cross-linked polymer comprising:

a first polymer selected from the group consisting of poly(methylmethacrylate), poly(styrene), poly(methacrylate), poly(urethane), and (poly)ester, polymers derived from acrylic acid, 4-vinyl pyridine, 2-vinyl pyridine, acrylonitrile, acrylamide, 2-acrylamido-2-methylpropane sulfonic acid, urocanic ethyl ester, (hydroxyethyl) methacrylate, and 2-(diethylamino)ethylmethacrylate, said first polymer cross-linked with a depolymerizable poly(ether) having the formula:

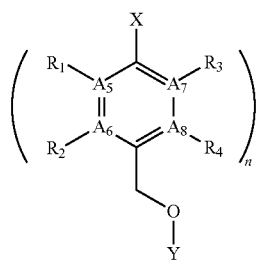

wherein n is between 2 and 1000;

wherein $A_5$, $A_6$, $A_7$, and $A_8$ are independently selected from the group consisting of nitrogen, oxygen, sulfur, and carbon, and wherein when the selection is other than sulfur or carbon the "R" group attached to the selection is not present;

wherein Y is selected from the group consisting of an ether, an ester, a carbamate, and a carbonate;

wherein X is selected from the group consisting of $R_3SiO$—, $(RO)_2B$—, $CH_2CHCH_2OCO_2$—, monosaccharide-O—, polysaccharide-O—, peptide-NH—, ortho-nitrobenzyl, ortho-nitrobenzyl carbamate, and

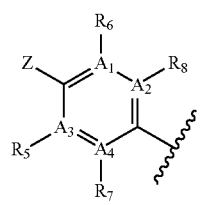

wherein $A_1$, $A_2$, $A_3$, and $A_4$ are independently selected from the group consisting of nitrogen, oxygen, sulfur, and carbon, and wherein when the selection is other than sulfur or carbon the "R" group attached to the selection is not present;

wherein $R_5$, $R_6$, $R_7$, and $R_8$ are selected independently from the group consisting of hydrogen, branched and straight chain alkyl having between one and thirty carbon atoms, and branched and straight chain aryl having between 2 and 30 carbon atoms; and wherein Z is selected from the group consisting of $(R)_3SiO$—, $(RO)_2B$—, $CH_2CHCH_2OCO_2$—, monosaccharide-O—, polysaccharide-O—, peptide-NH—, ortho-nitrobenzyl, and ortho-nitrobenzyl carbamate, wherein R is selected from the group consisting of hydrogen, straight-chain or branched alkyl between 1 and 30 carbon atoms, straight chain or branched aryl between 2 and 30 carbon atoms, an ether, and an ester; and wherein $R_1$ and $R_2$ are independently selected from the group consisting of hydrogen, branched and straight chain alkyl having between one and thirty carbon atoms, and branched and straight chain aryl having between 2 and 30 carbon atoms; and wherein $R_3$ and $R_4$ are independently selected from the group consisting of hydrogen, branched and straight chain alkyl having between one and thirty carbon atoms, and branched and straight chain aryl having between 2 and 30 carbon atoms; or $R_3$ and $R_4$, together with the carbon atoms to which they are attached, form an optionally substituted aromatic having the formula

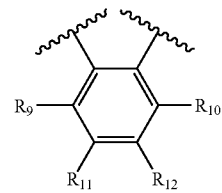

wherein $R_9$ and $R_{10}$ are independently selected from the group consisting of hydrogen, branched and straight chain alkyl having between one and thirty carbon atoms, and branched and straight chain aryl having between 2 and 30 carbon atoms; and wherein $R_{11}$ and $R_{12}$ are independently selected from the group consisting of hydrogen, branched and straight chain alkyl having between 1 and 30 carbon atoms, and branched and straight chain aryl having between 2 and 30 carbon atoms; or $R_{11}$ and $R_{12}$, together with the carbon atoms to which they are attached, form an optionally substituted aromatic having the formula

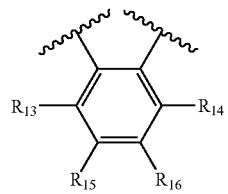

wherein $R_{13}$, $R_{14}$, $R_{15}$, and $R_{16}$ are independently selected from the group consisting of hydrogen, branched and straight chain alkyl having between 1 and 30 carbon atoms, and branched and straight chain aryl having between 2 and 30 carbon atoms; and wherein the first polymer and the depolymerizable ether are attached through a member of the group consisting of an amide, ester, imide, carbon bone, ether, or Huisgen cyclization, and wherein the attachment occurs through functionality at least two of $R_1$, $R_2$, $R_3$, $R_4$, and Y.

5. A film comprising a signal-responsive polymer of claim 1.

6. A container comprising a signal-responsive polymer of claim 1.

7. A medical apparatus comprising a signal-responsive polymer of claim 4.

8. A process for production of the signal-responsive polymer of claim 1, comprising:
reacting phthalaldehyde or phthalaldehyde derivative with a polymerizing compound selected from the group consisting of alkyl lithium reagents, alkyl grinard reagents, sodium alkoxides, lithium alkoxides, potassium alkoxides, and alkyl cuprate reagents to form a poly(phthalaldehyde); and
reacting the poly(phthalaldehyde) with an end-cap precursor selected from the group consisting of silyl chlorides, silyl triflates, alkyl chlorides, alkyl bromides, alkyl iodides, alkyl triflates, benzylic chlorides, benzylic bromides, benzylic iodides, benzylic triflates, isocyanates, chloroformates, chloroamides, allyl chlorides, allyl bromides, allyl iodides, allyl triflates, and the combination of triflic anhydride followed by an alcohol.

9. A process for the production of the signal-responsive polymer of claim 1, wherein X is

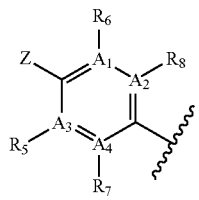

comprising:
in a first step, reacting phthalaldehyde with a compound having the formula:

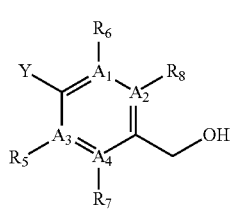

to form an intermediate, and
in a second step, in the presence of a catalyst, reacting the intermediate produced in the first step with a capping precursor selected from the group consisting of anhydrides, isocyanates, a chloroamide, an alkylating reagent, an acid chloride, an acid fluoride, and the combination of triflic anhydride followed by an alcohol.

10. The process of claim 9, wherein said catalyst is

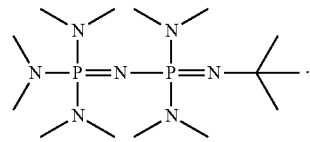 [SMILES: CN(C)P(=NC(C)(C)C)(N=P(N(C)C)(N(C)C)N(C)C)N(C)C]

11. A process for the production of the signal-responsive polymer of claim 2, comprising:
performing a step-wise synthesis in which monomer units are appended sequentially to the growing end of the polymer chain;
performing a metal-catalyzed polymerization reaction, wherein monomers contain both a benzylic alcohol and aryl halide functionality; or
performing a metal-catalyzed polymerization wherein two monomers are used simultaneously, and wherein a first monomer contains a trigger and a benzyl alcohol and serves as the terminus of a polymer chain, and wherein a second monomer contains both a benzylic alcohol and aryl halide functionality.

12. A method for detection of a substance in a sample, comprising:
in a sample in which the presence or absence of a substance is to be determined, adding an effective amount of a signal-responsive polymer of claim 1, wherein the signal-responsive polymer of claim 4 depolymerizes in the presence of the substance, and wherein the signal-responsive polymer depolymerizes into a plurality of monomers detectable by at least one of fluorescence and color change; and monitoring the sample for the presence of at least one of fluorescence and color change, wherein the presence of fluorescence and color change is indicative of the presence of the substance in the sample.

13. A method for creation of a depolymerization cascade, comprising:
exposing a first signal-responsive polymer to a signal that results in depolymerization of that polymer, wherein upon depolymerization the signal-responsive polymer creates at least one monomer that is a specific signal for depolymerization for at least one of the first signal-responsive polymer and at least one of a plurality of second signal-responsive polymers; and
exposing at least one of an additional quantity the first signal-responsive polymer and the second signal-responsive polymers to said at least one monomer, causing depolymerization of the exposed polymer and resulting in a depolymerization cascade.

14. A coating comprising a signal-responsive polymer of claim 1.

15. An adhesive comprising a signal-responsive polymer of claim 1.

16. The signal-responsive polymer of claim 1, wherein $R_1$ is H, $R_2$ is H, $R_3$ is H, and $R_4$ is H.

17. The signal-responsive polymer of claim 16, wherein n is between 100 and 1000.

* * * * *